United States Patent [19]

Rinehart, Jr. et al.

[11] 4,076,725

[45] Feb. 28, 1978

[54] DERIVATIVES OF STREPTOVARICIN ANSAMYCINS

[75] Inventors: Kenneth L. Rinehart, Jr., Urbana, Ill.; Frederick J. Antosz, Kalamazoo, Mich.; Kazuya Sasaki, Higashikurume, Japan

[73] Assignee: University of Illinois Foundation, Urbana, Ill.

[21] Appl. No.: 646,966

[22] Filed: Jan. 6, 1976

Related U.S. Application Data

[63] Continuation of Ser. No. 328,727, Feb. 1, 1973, abandoned.

[51] Int. Cl.² ............................................. C07D 319/08
[52] U.S. Cl. ................................. 260/340.3; 424/278
[58] Field of Search ....................................... 260/340.3

[56] References Cited

PUBLICATIONS

Rinehart et al., Journ. Amer. Chem. Soc., 97(1), pp. 196–198.

Chem. Abstracts 81: 295x, (1974).

*Primary Examiner*—Ethel G. Love
*Attorney, Agent, or Firm*—Merriam, Marshall & Bicknell

[57] ABSTRACT

New biologically active compounds derived by acylation and/or oxidative degradation of streptovaricin ansamycin materials, pharmaceutical compositions and therapeutic methods involving the same.

50 Claims, No Drawings

DERIVATIVES OF STREPTOVARICIN ANSAMYCINS

The invention described herein was made in the course of, or under, a grant from the National Institutes of Health, Department of Health, Education, and Welfare.

This application is a continuation of our application Ser. No. 328,727, filed Feb. 1, 1973, now abandoned.

BRIEF SUMMARY OF THE INVENTION

The present invention relates generally to new biologically active compounds derived from the streptovaricin ansamycin compounds, to new pharmaceutical compositions including such compounds, and to new therapeutic methods including the administration of such compositions. More particularly, the present invention relates to new compounds, some of which are referred to herein as streptovals, derived through oxidative degradation and/or acylation of streptovaricins, to pharmaceutical compositions containing these compounds and to therapeutic methods including administration of streptoval-containing pharmaceutical compositions.

BRIEF DESCRIPTION OF THE FORMULAE

The present invention will be better understood by reference to the following detailed description thereof along with the structural formulae wherein:

Formula 1 illustrates the compounds: streptovaricins A, B, C, D, E, G, and J;

Formula 2 illustrates the compound: streptovaricin F;

Formula 3 illustrates the compounds: streptovaricin A diacetate (streptovaricin G triacetate), streptovaricin A triacetate (streptovaricin G tetra-acetate), streptovaricin B diacetate (streptovaricin C triacetate and streptovaricin J diacetate), streptovaricin B triacetate (streptovaricin C tetra-acetate and streptovaricin J triacetate), streptovaricin D triacetate, streptovaricin D tetra-acetate, streptovaricin E diacetate, and streptovaricin E triacetate and the present invention;

Formula 4 illustrates the compounds: streptovaricin F diacetate and triacetate of the present invention;

Formula 5 illustrates a structural aspect common to all the new compounds of the present invention;

Formula 6 illustrates the compounds: streptovarone and prestreptovarone;

Formula 7 illustrates the compounds: streptoval A, streptoval A diacetate-A (streptoval G triacetate-A), and streptoval A diacetate-B (streptoval G triacetate B) of the present invention;

Formula 8 illustrates the compounds: isostreptoval A, isostreptoval A monoacetate (isostreptoval G diacetate), and isostreptoval A diacetate (isostreptoval G triacetate) of the present invention;

Formula 9 illustrates the compounds: streptoval B, streptoval B diacetate-A (streptoval C triacetate-A and streptoval J diacetate-A), and streptoval B diacetate-B (streptoval C triacetate-B and streptoval J diacetate-B) of the present invention;

Formula 10 illustrates the compounds: streptoval c, des-O-methyl streptoval C, and des-O-methyl streptoval C diacetate of the present invention;

Formula 11 illustrates the compounds: streptoval E, streptoval E diacetate-A, and streptoval E diacetate-B of the present invention;

Formula 12 illustrates the compounds: streptoval F, streptoval F diacetate-A, and streptoval F diacetate-B of the present invention;

Formula 13 illustrates the compounds: streptoval G, isostreptoval G and streptoval J of the present invention;

Formula 14 illustrates the compounds: streptovadienal C, streptovadienal E, streptovadienal F and streptovadienal G of the present invention.

In all of the compounds of Formulae 1–14 which are specifically named, Ac is an acetyl group. Compounds wherein Ac is an acyl group other than acetyl may be named according to standard rules of nomenclature.

DETAILED DESCRIPTION

The new compounds of the present invention are derived from streptovaricins A, B, C, D, E, F, G and J, which are members of the group of compounds termed streptovaricins. Streptovaricins are structurally related conpounds within the class of compounds containing an aliphatic ansa bridge — a bridge connecting two non-adjacent positions of an aromatic nucleus — for which class the term "ansamycins" has been employed.

Preparation of certain streptovaricins by fermentation from *Streptomyces spectabilis* (NRRL 2494) is discussed in U.S. Letters Patent No. 3,116,202. Generally stated, the fermentation process described therein give rise to an admixture of streptovaricins A, B, C, D, E, F, G, and J, the principal component of which is streptovaricin C. Structures (Formulae 1 and 2) were assigned to these compounds by the present inventors and their colleagues (*J. Antibiot.*, 25, 71 (1972); *J. Amer. Chem. Soc.*, 93, 6273 (1971); ibid., 93, 6275 (1971)).

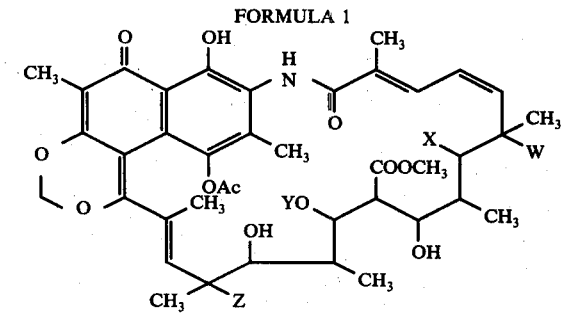

FORMULA 1

STREPTOVARICIN A
Wherein: W is OH, X is OH; Y is Ac, and Z is OH.
STREPTOVARICIN B
Wherein: W is H; S is OH; Y is Ac, and Z is OH.
STREPTOVARICIN C
Wherein: W is H; X is OH; Y is H, and Z is OH.
STREPTOVARICIN D
Wherein: W is H; X is OH; Y is H, and Z is H.
STREPTOVARICIN E
Wherein: W is H; X is O=; Y is H, and Z is OH.
STREPTOVARICIN G
Wherein: W is OH; X is OH; Y is H, and Z is OH.
STREPTOVARICIN J
Wherein: W is H; X is OAc; Y is H, and Z is OH.

FORMULA 2

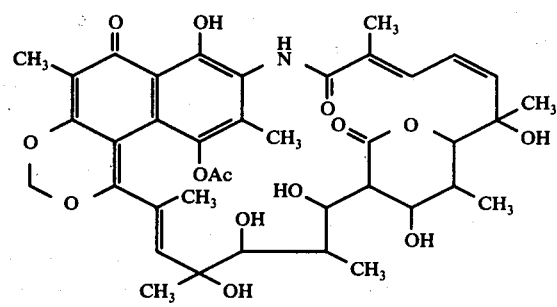

Several of the streptovaricins are known to have antibacterial activity, especially against gram-positive bacteria (*Amer. Rev. Tuberc. Pulm. Dis.*, 75, 576 (1957)), and are known to repress *Mycobacterium tuberculosis*, (ibid., 75, 588 (1957)) and murine leprosy (ibid., 79, 673 (1957)). The proposed mode of action of the streptovaricins as antibacterial agents is through blockage of DNA-directed RNA polymerase (*J. Antibiot.*, 21, 63 (1968); *Biochem. Biophys. Acta*, 157, 222 (1968)).

Some streptovaricins have also been shown to possess some anti-viral activity (*J. Virol.*, 6, 485 (1970); *Biochem. Biophys. Res. Commun.*, 42, 230 (1971)).

New compounds of the present invention exhibit antibacterial and other biological activity as great as and in some instances greater than the streptovaricins from which they are prepared. Like the streptovaricins they are expected to be substantially non-toxic in pharmaceutical preparations.

The following examples illustrate the preparation of the compounds of the present invention by oxidative degradation and/or acylation.

EXAMPLE I

PREPARATION OF ACYLATED STREPTOVARICINS

FORMULA 3

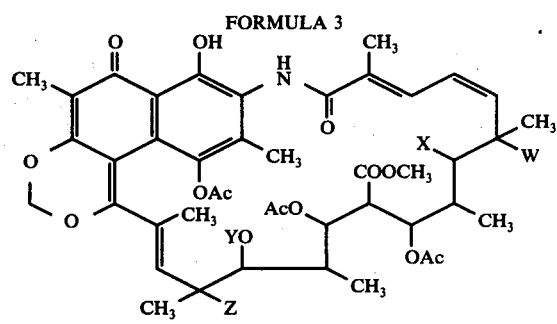

STREPTOVARICIN A DIACETATE (STREPTOVARICIN G TRIACETATE)
Wherein: w is OH; X is OAc; Y is H, and Z is OH.
STREPTOVARICIN D TRIACETATE
Wherein: W is H; X is OAc; Y is H, and Z is H.
STREPTOVARICIN B DIACETATE (STREPTOVARICIN C TRIACETATE) (STREPTOVARICIN J DIACETATE)
Wherein: W is H; X is OAc; Y is H, and Z is OH.
STREPTOVARICIN A TRIACETATE (STREPTOVARICIN G TETRA-ACETATE)
Wherein: W is OH; X is OAc; Y is Ac, and Z is OH.
STREPTOVARICIN B TRIACETATE (STREPTOVARICIN C TETRA-ACETATE)
Wherein: W is H; X is OAc; Y is Ac, and Z is OH.
STREPTOVARICIN D TETRA-ACETATE
Wherein: W is H; X is OAc; Y is Ac, and Z is H.
STREPTOVARICIN E DIACETATE
Wherein: W is H; X is O=; Y is H, and Z is OH.
STREPTOVARICIN E TRIACETATE
Wherein: W is H; X is =O; Y is Ac, and Z is OH.

A. PREPARATION OF STREPTOVARICIN A DIACETATE

A mixture of 500 mg. (0.605 mmol.) of streptovaricin A, 10 ml. of pyridine and 30 ml. of acetic anhydride was stirred at room temperature for 24 hours. The mixture was then poured into 500 ml. of cold water. The resulting solution was extracted with three 30-ml. portions of ethyl acetate. The organic extracts were combined, dried over magnesium sulfate, and filtered. The filtrate was taken to dryness in vacuo, and the residue was chromatographed over silica gel, eluting with chloroform/methanol (98/2: v/v). Fractions containing streptovaricin A diacetate were combined, dissolved in a small volume of 1-chlorobutane, and hexane was added. The resulting solid was filtered to yield 295 mg. (50%) of an orange powder; which analyzed as follows:

M.P. 201°–203° C;
Specific Rotation $[\alpha]_D^{27}$ + 498° (c 0.24, CHCl$_3$);
IR (CHCl$_3$) 3500, 3410, 2990, 2920, 1750, 1710, 1650, 1600, 1580, 1530, 1480, 1430, 1370, 1330, 1245, 1190 cm$^{-1}$;
Analysis: Calculated for $C_{46}H_{59}NO_{18}$: C, 60.44; H, 6.51; N, 1.53. Found: C, 60.16; H, 6.39; N, 1.61.

The structure assigned to streptovaricin A diacetate is set out in formula 3. It is to be noted that due to the structural similarity between streptovaricin A and streptovaricin G, the streptovaricin A diacetate product of the above two-mole addition of acetate is identical to the streptovaricin G triacetate product of the following, analogous, three-mole addition preparation wherein streptovaricin G is the starting material.

B. PREPARATION OF STREPTOVARICIN G TRIACETATE

A mixture of 78.5 mg. (0.10 mmol.) of streptovaricin g, 3 ml. of pyridine, and 10 ml. of acetic anhydride was stirred at room temperature for 24 hours. The mixture was then poured into 300 ml. of cold water. The resulting solution was extracted with two 30-ml. portions of ethyl acetate. The organic extracts were combined, dried over magnesium sulfate, and filtered. The filtrate was taken to dryness in vacuo and the resulting red oil was chromatographed over silica gel, eluting with chloroform/methanol (98/2: v/v). Fractions containing the major conponent were combined and yielded a yellow powder from ethyl acetate/hexane, which was identical in all respects with streptovaricin A diacetate (M.P. 202°–204° C, mixture melting point with authentic streptovaricin a diacetate, 202°–204° C).

C. PREPARATION OF STREPTOVARICIN C TRIACETATE (STREPTOVARICIN B DIACETATE AND STREPTOVARICIN J DIACETATE) AND TETRAACETATE (STREPTOVARICIN B TRIACETATE AND STREPTOVARICIN J TRIACETATE)

A mixture of 3.0 g. (3.9 mmol.) of streptovaricin C, 20 ml. of pyridine and 120 ml. of acetic anhydride was stirred at room temperature for 25 hours. The mixture was then poured into 400 ml. of ice-water. The resulting solution was extracted with three 100-ml. portions of ethyl acetate. The combined organic extract was washed with two 100-ml. portions of water, followed by 100 ml. of a saturated sodium chloride solution, and was then dried over magnesium sulfate and filtered. The filtrate was taken to dryness in vacuo to yield 3.4 g. of an orange-red solid which was chromatographed over 250 g. of silica gel, eluting with increasing amounts of acetone in benzene. Elution with benzene/acetone (4/1: v/v) yielded 1.65 g. of streptovaricin C triacetate, which was crystallized from methylene chloride ether to yield 1.28 g. (32%) of crystalline streptovaricin C triacetate, which analyzed as follows:

M.P. 228.5°–229.5° C;

IR (CHCl$_3$) 3450, 3300, 3030, 3010, 2990, 2940, 1740 (broad), 1660, 1605, 1580, 1535, 1485, 1435, 1370, 1330, 1235 (broad), 1190 cm$^{-1}$;

UV (ethanol) max 208 ($\epsilon$19,000), 245 ($\epsilon$30,000), 263 sh ($\epsilon$24,500), 315 ($\epsilon$9,700), 427 nm ($\epsilon$8,800);

NMR (220 HMz) (CDCl$_3$) $\delta$0.92 (d,3,J=7 Hz, CHCH$_3$), 1.06 (d,3,J=7 Hz, CH–CH$_3$), 1.11 (d,3,J=7 Hz, CH–CH$_3$), 1.16 (s,3), 1.88 (s,3), 1.95 (s,3), 1.96 (s,3), 1.97 (s,3), 202 (s,3) 2.12 (s,3), 2.24 (s,3), 2.28 (s,3), 2.71 (s,1,C-OH), 2.85 (d,1,J=4 Hz, HO-CH), 3.08 (d,1,J=8 Hz, CH-CO$_2$CH$_3$), 3.35–3.55 (m,1,C=CH-CH-CH$_3$), 3.73 (s,3,CO$_2$CH$_3$), 5.19 (d,1,J=10 Hz, CH-OAc), 5.55–5.65 (m,2 2 CH-OAc), 5.61 (d,1,J=5 Hz, O-CH-O), 6.01 (bs,1,C=CH), 6.03 (t,1,J,=11 Hz, HC=CH-CH, 6.27 (d,1,J=5 Hz, O-CH-O), 6.80 (t,1,J=11 Hz, CH=CH-CH=C), 8.20 (d,1,J=11 Hz, C=CHCH=), 8.28 (s,1, —CO—NH—), 14.20 (s,1,C=C-OH);

(220 MHz) (pyridine-d$_5$) $\delta$0.98 (d,3,J=7 Hz, CH-CH$_3$), 1.07 (d,3,J=7 Hz, CH-CH$_3$), 1.23 (d,3,J=7 Hz, CH-CH$_3$), 1.64 (s,3), 1.86 (s,3), 1.93 (s,3), 1.98 (s,3), 2.04 (s,3), 2.19 (s,3), 2.32 (s,3), 2.53 (s,3), 2.70 (s,3), 3.4–3.6 (m,1,C=CH-CH$_3$), 3.68 (s,1,CH-OH), 3.72 (s,3,-CO$_2$CH$_3$), 3.92 (d,1,J=10 Hz, CH-CO$_2$CH$_3$), 4.93 (d,1,J=10 Hz, CH-OAc), 5.05 (S,1,C-OH), 5.21 (d,1,J=5 Hz, O-CH-O), 5.5–5.8 (m,3), 6.02 (d,1,J=5 Hz, O-CH-O), 6.43 (bs,1,C=CH), 6.47 (t,1,J=11 Hz), 7.61 (s,1,—CO—NH—), 7.92 (d,1,J=11 Hz, (C=CHCH=);

Mass Spec. (70 eV) m/e (rel intensity) 895 (M$^{30}$) (8), 880 (1), 877 (1), 853 (3), 836 (4), 835 (3), 820 (8), 802 (4), 775 (3), 760 (5), 742 (10), 715 (6), 418 (12), 390 (52), 339 (42), 325 (33), 324 (66), 323 (41), 322 (46), 321 (29), 320 (28), 319 (33), 308 (29), 300 (32), 299 (34), 298 (97), 297 (100), 296 (50), 283 (25), 282 (28), 269 (62), 225 (25), 254 (18), 253 (24), 227 (29), 187 (26), 173 (43), 171 (24), 165 (29), 161 (24), 159 (59), 157 (25), 153 (31), 151 (44), 147 (20), 145 (39), 143 (30), 135 (48), 133 (57), 123 (25), 122 (25), 121 (26), 119 (42), 107 (45), 105 (73), 95 (62), 93 (68), 91 (72), 79 (59), 77 (53), 69 (55), 67 (48), 65 (23), 60 (46), 55 (67);

Analysis: Calculated for C$_{46}$H$_{57}$NO$_{17}$: C, 61.67; H, 6.41; N, 1.56. Found: C, 61.39; H, 6.39; N, 1.60.

Continued elution, with benzene/acetone (3.1: v/v) yielded 498 mg. of slightly impure streptovaricin C tetraacetate which was purified by precipitation from ethyl acetate with n-hexane to yield 396 mg. (11%) of streptovaricin C tetra-acetate as an orange amorphous solid which analyzed as follows:

M.P. 183°–185° C;

NMR (100 MHz) (CDCl$_3$) $\delta$0.18 (d,3,J=7 Hz, CH-CH$_3$), 1.08 (d,6,J=7 Hz, 2 CH—CH$_3$), 1.29 (s,3), 1.97 (bs,15), 2.12 (s,3), 2.15 (s,3), 2.27 (s,3), 2.35 (s,3), 2.6–3.3 (m,2), 3.4–3.7 (m,1), 3.87 (s,3,CO$_2$CH$_3$), 4.5–5.0 (m,3), 5.1–5.4 (m,1), 5.27 (d,1,J=5 Hz, O-CH-O), 5.54 (t,1,J=11 Hz, CH=CH-CH), 5.67 (s,1,C=CH), 5.89 (d,1,J=5 Hz, O-CH-O), 6.41 (t,1,J=11 Hz, CH=CH-CH), 7.77 (d,1,J=11 Hz, C=CHCH=), 7.85 (s,1,CO-NH), 14.02 (s,1,C=C-OH);

(100 MHz) (pyridine-d$_5$) $\delta$0.89 (d,3,J=7 Hz, CH-CH$_3$), 1.11 (d,3,J=7 Hz, CH-CH$_3$), 1.25 (d,3,J=7 Hz, CH-CH$_3$), 1.62 (s,3), 1.77 (s,3), 2.00 (s,9), 2.12 (s,3), 2.15 (s,3), 2.38 (s,3), 2.54 (s,3), 2.47 (s,3), 2.9–3.3 (m,1), 3.3–3.7 (m,1), 3.72 (s,3), 3.91 (d of d,1,J=2 and 11 Hz, CH-CO$_2$CH$_3$), 5.07 (d of d,1,J=4 and 11 Hz, CH-OAc), 5.2–5.4 (m,2), 5.32 (d,1,J=5 Hz, O-CH-O), 5.4–5.7 (m,1), 5.72 (t,1,J=11 Hz, CH=CH-CH), 6.07 (d,1,J=5 Hz, O-CH-O), 6.20 (s,1,CH=C), 6.50 (t,1,J=11 Hz, CH=CH-CH), 7.81 (d,1,J=11 Hz, C=CHCH=), 9.01 (s,1,CO-NH);

Mass Spectrum (70 eV) m/e (rel intensity) 937 (M$^+$) (0.1), 919 (0.1), 877 (0.3), 859 (0.5), 817 (1.7), 803 (2), 802 (4.2), 801 (1), 800 (1), 799 (1), 758 (2.7), 742 (4.3), 730 (7.7), 698 (1.4), 682 (1.8), 666 (1.1), 638 (1), 622 (1.3), 606 (1.3), 507 (1), 484 (1.7), 390 (6), 339 (7), 324 (8), 323 (5), 322 (11), 321 (16), 320 (8), 297 (30), 269 (6), 244 (5), 231 (6), 178 (10), 165 (13), 151 (17), 133 (13), 122 (18), 110 (19), 105 (14), 95 (14), 93 (19), 91 (21), 79 (18), 77 (22), 43 (100);

Analysis: Calculated for C$_{48}$H$_{59}$NO$_{18}$: C, 61.46; H, 6.34; N, 1.49. Found: C, 61.25; H, 6.48; N, 1.55.

The structures assigned to streptovaricin C tri and tetra-acetates are set out in Formula 3. Again it will be noted that the products of the above three- and four-mole addition of acetate to streptovaricin C are respectively identical to the streptovaricin B di- and triacetate products of the following analogous two- and three-mole addition to streptovaricin B and the streptovaricin J di- and triacetate products to the two- and three-mole addition to streptovaricin J.

D. PREPARATION OF STREPTOVARICIN D DI- AND TRIACETATE

A mixture of 240 mg. (0.296 mmol.) of streptovaricin B, 5 ml. of pyridine and 10 ml. of acetic anhydride was stirred at room temperature for 24 hours. The mixture was then poured into ice-water. The resulting solution was extracted with two 50-ml. portions of ethyl acetate. The combined extracts were backwashed with 50 ml. of a saturated sodium chloride solution, dried over sodium sulfate and filtered. The filtrate was taken to dryness in vacuo, and the resultant red oil was chromatographed over silica gel, eluting with chloroform/methanol (99/1: v/v). Fractions containing streptovaricin B diacetate were combined and rechromatographed over silica gel eluting with chloroform/methanol (98/2: v/v). Fractions containing the diacetate derivative were combined and crystallized from ethyl acetate/n-hexane to yield 85 mg. (32%) of crystalline material which was identical in all respects with streptovaricin C triacetate (M.P. 230°–231° C, mixture melting point with authentic streptovaricin C triacetate showed no depression, M.P. 230°–231° C).

Continued elution of the first column yielded a small amount of a second material, streptovaricin B triacetate, which was identified by thin layer chromatography as identical to streptovaricin C tetra-acetate.

E. PREPARATION OF STREPTOVARICIN J DIACETATE

A solution of 2.72 mg. (0.335 mmol.) of streptovaricin J, 2 ml. of pyridine and 5 ml. of acetic anhydride was stirred at room temperature for 24 hours. The mixture was poured into ice-water, and the resulting suspension was extracted with two 40-ml. portions of ethyl acetate. The extracts were combined, dried over magnesium sulfate and filtered. The filtrate was taken to dryness in vacuo and the residue was thoroughly dried under high vacuum. The residue was chromatographed over 25 g. of silica gel, eluting with benzene/acetone (9/1: v/v) until streptovaricin J diacetate began to elute. The column was then eluted with 200 ml. of benzene/acetone (85/15: v/v) followed by benzene/acetone (4/1: v/v) until elution was stopped.

Fractions containing streptovaricin J diacetate were combined and crystallized from ethyl acetate-hexane to yield 35 mg. (12%) of crystalline streptovaricin J diacetate which had a melting point of 220.5°-222° C. This material was determined to be identical with streptovaricin C triacetate, M.P. 221.5°-223° C; mixture melting point 220°-222° C.

The above procedures, when applied to streptovaricins D and E, will give rise to the products (shown in Formula 3), streptovaricin D triacetate, streptovaricin D tetra-acetate, streptovaricin E diacetate and streptovaricin E triacetate. Similarly, when the above procedures are applied to streptovaricin F (Formula 2) the resulting products are streptovaricin F diacetate and streptovaricin F triacetate (Formula 4).

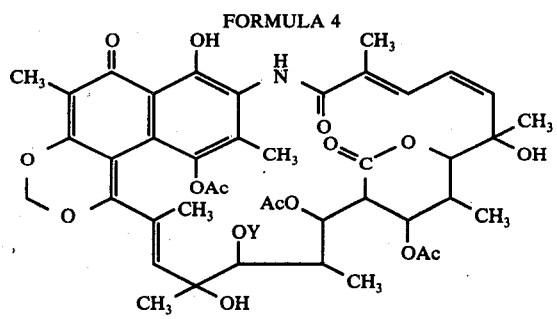

FORMULA 4

Streptovaricin F Diacetate (Y is H)
Streptovarican F Triacetate (Y is Ac)

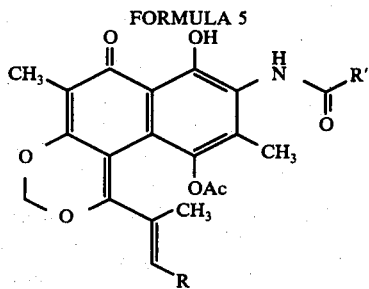

FORMULA 5

Formula 5, above, illustrates a structural aspect common to all new compounds of the present invention.

EXAMPLE II

Preparation of Streptovarone

Into a 5-liter three-necked Morton flask (with creased sides) equipped with a mechanical stirrer were placed 25 g. of 70% streptovaricin C, 200 ml. of methylene chloride, 800 ml. of ether, 1 g. of osmium tetroxide, 150 ml. of ether, a solution of 43 g. of sodium metaperiodate in 700 ml. of water, 2 ml. of pyridine, and 50 ml. of dioxane. The flask was covered with aluminum foil and stirring was commenced. After 9 hours, 50 ml. of dioxane and 400 ml. of ether were added. After 48 hours the stirring was stopped, the reaction mixture was poured into a 4-liter separatory funnel, and the phases were separated. The aqueous phase was extracted twice with 300-ml. portions of methylene chloride. These extracts were added to the organic phase and the total solution was saturated with hydrogen sulfide and allowed to stand for 30 minutes. One or two filtrations through a fluted paper filter removed the osmium sulfide precipitate. The red solution was then dried over sodium sulfate and filtered, and the solvent was removed on the rotary evaporator.

A 600-ml. sintered glass funnel was packed with silica gel in 1% methanol in chloroform and the reaction mixture was chromatographed over this column. The first fractions contained streptovarone with a small amount of a more polar impurity. The remainder of the material on the column consisted of a complex mixture and was discarded. The solution of streptovarone was taken to dryness on the rotary evaporator, dissolved in a minimum amount of methylene chloride, filtered, and diluted with at least two volumes of ether. The flask was allowed to stand at room temperature for several hours while crystallization occurred. The solution was filtered and 2.3 g. of streptovarone was collected. The solution was taken to dryness on the rotary evaporator, and the non-crystalline residue was rechromatographed in the same manner over a smaller silica column. The streptovarone fraction was worked up and crystallized from methylene chloride and ether to yield approximately 1 g. The total yield, assuming 70% streptovaricin C, was around 30%.

The structure assigned to streptovarone is set out in Formula 6.

FORMULA 6

(A) STREPTOVARONE WHEREIN: R is [structure with C=O, CH₃]; and R¹ is [structure with CH₃, C=O];

(B) PRESTREPTOVARONE WHEREIN: R is [structure with C=O, CH₃]; and R¹ is [structure with CH₃, C=O, CH₃]

EXAMPLE III

PREPARATION OF PRESTREPTOVARONE

Streptovaricin A (5.0 g.) was dissolved in ethanol (400 ml.) and treated with a solution of sodium metaperiodate in water (350 ml.) for 24 hr. at room temperature. The reaction material was filtered and extracted with ether, the extracts being subsequently washed with saturated salt solution and dried over anhydrous sodium sulfate. Solvent removal gave a black tar which was grossly chromatographed on a 500-g. silica gel sintered glass funnel column and finely chromatographed on a 90-cm. by 4-cm. silica gel tapered column. In each case, 5% methanol in chloroform was the eluant. The isolated material weighed 2.04 g. (62%) and analyzed as follows:

M.P. 194°–197° C;

Analysis: Calculated for $C_{29}H_{29}NO_9$ 535.5; C, 65.04; H, 5.46; N, 2.62. Found: 535; C, 65.07; H, 5.55; N, 2.65.

The structure assigned to prestreptovarone is set out in Formula 6.

EXAMPLE IV

PREPARATION OF STREPTOVAL A AND ISOSTREPTOVAL A

Streptovaricin A, 827 mg. (1.0 mmol.), and sodium metaperiodate, 231 mg. (1.0 mmol.), were dissolved in 100 ml. of 25% aqueous ethanol. The resulting solution was stirred in the dark at 32° C for 15 hours. Organic products were isolated by removal of the ethanol solvent in vacuo, and the remaining aqueous phase was partitioned with ethyl acetate. The ethyl acetate solution was evaporated to dryness in vacuo. A bright red residue was obtained.

A mixture of streptoval A and isostreptoval A was obtained from this residue by preparative thin layer chromatography on silica gel using chloroform/methanol (92/8: v/v) as the elution solvent. The poorly resolved bands corresponding to streptoval A and isostreptoval A were removed, the compounds were eluted from the silica gel with ethyl acetate, and the ethyl acetate was removed by evaporation in vacuo. The mixture so obtained was dissolved in benzene, spotted on preparative thin layer plates as described above, and eluted twice with chloroform/methanol (92/8: v/v).

An orange band corresponding to isostreptoval A was removed and eluted with ethyl acetate. This material was rechromatographed as above to yield 119 mg. (14.4%) of an orange red glass, which analyzed as follows:

UV (ethanol) max 244 ($\epsilon$32,400); 289 ($\epsilon$28,000); 339 sh ($\epsilon$14,850); 444 nm ($\epsilon$13,450);

IR (neat) 3475, 2990, 2940, 1760, 1740, 1620, 1500, 1440, 1375, 1340, 1240, 1195 cm$^{-1}$;

Molecular Weight: Calculated for $C_{42}H_{51}NO_{16}$: 825.3202 Found: 825.3194

A red band corresponding to streptoval A was removed and eluted with ethyl acetate. This material was rechromatographed as above to yield 5 mg (0.6%) of a red glass which analyzed as follows:

UV (ethanol) max 212 ($\epsilon$33,200), 248, ($\epsilon$43,000), 264 sh ($\epsilon$38,800), 326 ($\epsilon$17,400), 450 nm ($\epsilon$12,800);

IR (neat) 3410, 2990, 1758, 1740, 1625, 1590, 1500, 1430, 1370, 1330, 1245, 1190 cm$^{-1}$;

Molecular Weight: Calculated for $C_{42}H_{51}NO_{16}$: 825.3202 Found: 825.3194

The structure assigned to streptoval A is set out in Formula 7. The structure assigned to isostreptoval A is set out in Formula 8.

FORMULA 7

(A) STREPTOVAL A

WHEREIN: R is [structure with C=O, CH₃];

and R¹ is [structure with CH₃, CH₃, CH₃, HO, O, OH, OH, CH₃, COOCH₃, OAc]

-continued (B) STREPTOVAL A DIACETATE-A
(STREPTOVAL G TRIACETATE-A)

WHEREIN: R is 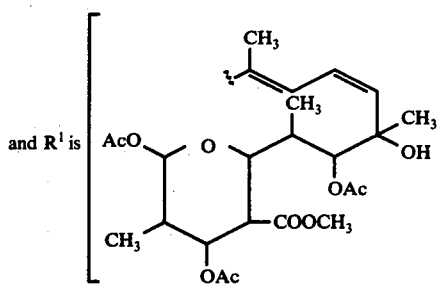

and R¹ is (C) STREPTOVAL A DIACETATE-B
(STREPTOVAL G TRIACETATE-B)

WHEREIN: R is and R¹ is 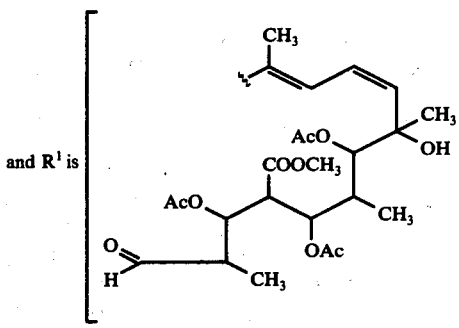

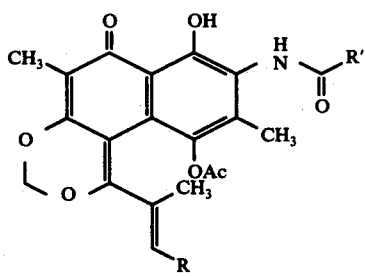

(A) ISOSTREPTOVAL A, WHEREIN:

R is and R¹ is (B) ISOSTREPTOVAL A MONOACETATE
(ISOSTREPTOVAL G DIACETATE) WHEREIN:

-continued

R is 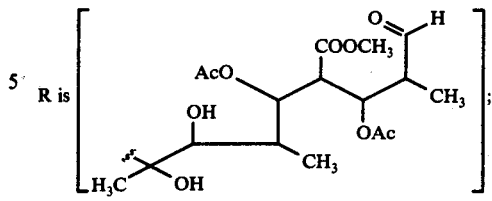

and R¹ is 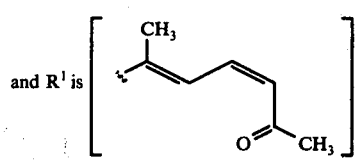

(C) ISOSTREPTOVAL A DIACETATE
ISOSTREPTOVAL G TRIACETATE) WHEREIN:

R is 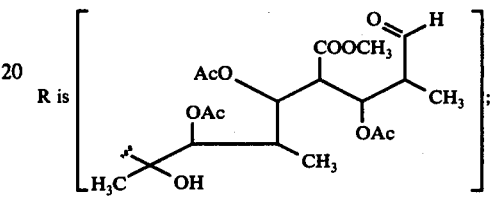

and R¹ is 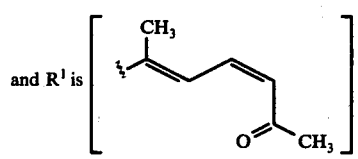

EXAMPLE V

PREPARATION OF STREPTOVAL B

A mixture of 131 mg. (0.161 mmol.) of streptovaricin B, 692 mg. (3.23 mmol.) of sodium periodate, 10 ml. of ethanol and 10 ml. of water was stirred at room temperature. The reaction flask was wrapped with aluminum foil. After 92.5 hours most of the ethanol was removed in vacuo. The resulting aqueous solution was diluted with 30 ml. of water and extracted with two 30-ml. portions of ethyl acetate. The organic extracts were combined, dried over magnesium sulfate, and filtered. The filtrate was taken to dryness in vacuo to yield a red-orange glass which was purified by chromatographing it over 20 g. of silica gel. The column was eluted in order with 50 ml. of benzene/acetone (9/1: v/v), 50 ml. of benzene/acetone (88/12: v/v), 50 ml. of benzene/acetone (86/14: v/v) and then with benzene-/acetone (84/16: v/v) until all of the streptoval B had been eluted. No fractions were collected until the first dark colored band began to elute. The second dark band to elute was streptoval B.

The combined fractions containing streptoval B were further purified via perparative thin layer chromatography [20 × 20 cm; 1 mm. PF 254]. The plate was developed four times in benzene/acetone (85/15: v/v) followed by three times in benzene/acetone (4/1: v/v). The major red-orange band was removed, eluted with ethyl acetate/ethanol (1/1: v/v) and filtered. The filtrate was taken to dryness in vacuo to yield 56 mg. (43%) of a red-orange glass which was lyophilized from benzene to yield orange colored amorphous streptoval B which analyzed as follows:

M.P. 132°–137° C;

UV (EtOH) 216 ($\epsilon$ 22,700), 250 (sh) ($\epsilon$ 32,100), 263 ($\epsilon$ 32,900), 330 ($\epsilon$ 10,900), 452nm ($\epsilon$ 9,600);

IR (KBr) 3420, 2970, 2930, 2880, 1765 (sh), 1735, 1685, 1620, 1590, 1495, 1440, 1365, 1337, 1243, 1195, 1135, 1095, 1040, 995 cm$^{-1}$;

NMR (220 MHz) (CDCl$_3$) 0.94 (d,3,J=7 Hz, (CH-CH$_3$), 1.01 (d,3,J=7 Hz, CH-CH$_3$), 1.13 (d,3,J=7 Hz, CH-CH$_3$), 1.99 (s,3), 2.04 (bs,3), 2.07 (s,3), 2.15 (s,3), 2.18 (s,3), 2.20 (s,3), 3.07 (t,1,J=11 Hz, CH-CO$_2$CH$_3$), 3.1 (m,1,C=C-CH-CH$_3$), 3.37 (d of d,1,J=3 and 8 Hz, CH-OH), 3.71 (s,3,CO$_2$CH$_3$), 4.45 (d of d,1,J=4 and 11 Hz, CH-OH), 5.11 (bs,1,O-CH-OH), 5.21 (bs,1,O-CH-O), 5.51 (d of d,1,J=5 and 10 Hz, CH-OAc), 5.85 (bs,1,O-CH-O), 5.94 (t,1,J=11 Hz, CH=CH-CH), 6.45 (t,1,J=11 Hz, CH=CHCH), 6.75 (bs,1,CH=C-CH$_3$), 7.43 (d,1,J=11 Hz, C=CHCH=), 7.75 (s,1, NH=CO), 14.10 (s,1, C=C-OH);

Mass Spectrum (70 eV) m/e (rel intensity) 731 (M-78) (0.4), 689 (0.3), 671 (0.7), 639 (0.7), 629 (0.9), 613 (1.7), 593 (0.7), 592 (0.7), 571 (1.2), 489 (1), 461 (2.4), 460 (2.5), 432 (26), 390 (20), 366 (9), 363 (2.2), 350 (3), 348 (3.6), 340 (8), 339 (28), 338 (11), 325 (1), 324 (16), 323 (6), 322 (5), 321 (7), 320 (2.3), 311 (2), 310 (1.2), 309 (1.7), 308 (2.5), 307 (1.7), 306 (1), 298 (8), 297 (30), 296 (7), 282 (3.3), 269 (10), 254 (1.9), 253 (1.9), 211 (2.8), 179 (4.5), 153 (38), 151 (8), 150 (10), 149 (7), 135 (5), 133 (8), 125 (5), 123 (7), 122 (8), 121 (6), 114 (7), 111 (7), 110 (6), 107 (9), 105 (10), 95 (13), 93 (9), 91 (12), 87 (7), 83 (6), 82 (6), 81 (6), 79 (12), 77 (11), 74 (20), 60 (12), 67 (7), 60 (100), 55 (17), 45 (98), 44 (47), 43 (98), 42 (42), 41 (15), 39 (8).

Analysis: Calculated for C$_{42}$H$_{51}$NO$_{15}$: C, 62.27; H, 6.35; N, 1.73. Found: C, 61.38; H, 6.40; N, 1.97.

The structure assigned to streptoval B is shown in Formula 9.

FORMULA 9

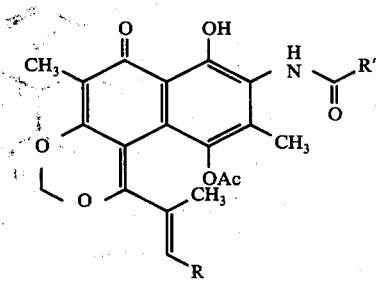

(A) STREPTOVAL B WHEREIN:

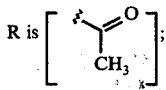

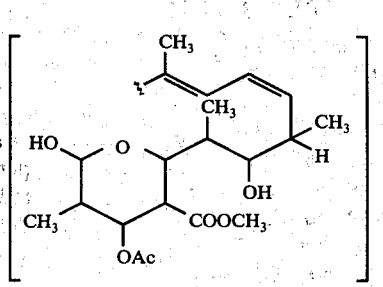

(B) STREPTOVAL B DIACETATE-A
(STREPTOVAL C TRIACETATE-A and STREPTOVAL J DIACETATE A) WHEREIN:

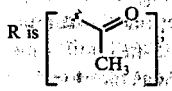

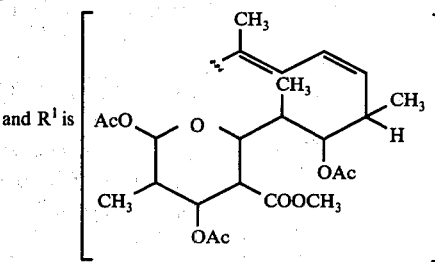

(C) STREPTOVAL B DIACETATE-B
(STREPTOVAL C TRIACETATE-B and STREPTOVAL J DIACETATE-B) WHEREIN:

R is 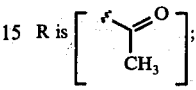;

and R$^1$ is 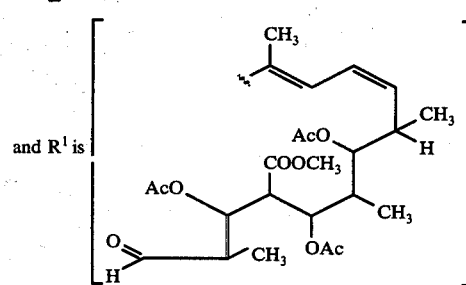

EXAMPLE VI

PREPARATION OF STREPTOVAL C

A mixture of 4.3 g. (20.2 mmol.) of sodium metaperiodate in 50 ml. of water was added to a stirred solution of 768 mg. (1.0 mmol.) of streptovaricin C in 50 ml. of t-butyl alcohol. The reaction flask was wrapped with aluminum foil to protect the reactants from light. After 9 hours the reaction mixture was diluted with 200 ml. of water and extracted with three 50-ml. portions of ethyl acetate.

The organic extracts were combined, washed with 50 ml. of a saturated sodium chloride solution, dried over magnesium sulfate, filtered, and taken to dryness in vacuo. The resultant reddish-orange residue was chromatographed over 60 g. of silica gel, using chloroform/methanol (97/3: v/v) as elution solvent. Fractions containing streptoval C were combined and then dissolved in hot 1-chlorobutane containing methylene chloride.

The solid which formed on standing was filtered, yielding 496 mg. of wine-colored streptoval C, m.p. 136°–139° C. The mother liquor yielded an additional 84 mg. of streptoval C for a total yield of 580 mg. (75%). The resultant material contained some 1-chlorobutane. Solvent-free material was obtained by dissolving in 1-chlorobutane and precipitating the material with hexane. The material analyzed as follows:

M.P. 140°–143° C;

UV (methanol) max 208 ($\epsilon$ 28,700), 250 ($\epsilon$ 37,000), 260 (sh) ($\epsilon$ 36,900), 328 ($\epsilon$ 14,000), 450nm ($\epsilon$ 11,000).

IR (KBr) 3430, 2970, 2930, 1766, 1730, 1685, 1272, 1195 cm$^{-1}$.

NMR (220 MHz) (CDCl$_3$) 0.96 (d,3,J=7 Hz, CH-CH$_3$), 0.98 (d,3,J=7 Hz, CH-CH$_3$), 1.10 (d,3,J=7 Hz, CH-CH$_3$), 1.98 (s,3), 2.05 (s,3), 2.13 (s,3), 2.16 (s,3), 2.19 (s,3), 2.26 (s,3), 2.85 (t,1,J=10.5 Hz, CH-CO$_2$CH$_3$), 3.12 (m,1,CH-CH$_3$), 3.30 (d of d,1,J=3 and 8 Hz, CH-OH), 3.73 (s,3,CO$_2$CH$_3$), 4.37 (m,2), 5.11 (bs,1,O-C<u>H</u>-OH), 5.23 (bs,1,O-C<u>H</u>-O), 5.84 (bs,1,O-C<u>H</u>-O), 5.92 (t,1,J=11 Hz, CH=C<u>H</u>-CH), 6.44 (t,1,J=11 Hz, C<u>H</u>=CHCH=), 6.59 (bs,1,C<u>H</u>=C-CH₃), 7.40 (d,1,J=11 Hz, C=C<u>H</u>CH=), 7.79 (s,1,N<u>H</u> CO), 14.15 (s,1,C=C-OH);

Mass Spectrum (70 eV) m/e (rel intensity) 689 (M-78) (0.3), 671 (0.3), 647 (0.3), 639 (0.2), 629 (0.3), 613 (1.7), 595 (0.8), 571 (1.3), 555 (1), 553 (0.8), 537 (1.4), 522 (1.2), 461 (4), 433 (12), 432 (45), 431 (30), 430 (31), 417 (15), 416 (50), 414 (12), 391 (11), 390 (38), 389 (26), 388 (44), 374 (13), 366 (37), 348 (10), 399 (72), 338 (27), 325 (12), 324 (53), 323 (23), 322 (33), 321 (25), 298 (22), 297 (82), 296 (20), 269 (30), 153 (32), 150 (27), 134 (22), 133 (28), 125 (14), 123 (22), 122 (22), 107 (25), 106 (45), 105 (52), 91 (91), 79 (36), 77 (35), 69 (25), 44 (100).

Analysis: Calculated for $C_{40}H_{49}NO_{14}$: C, 62.52; H, 6.43; N, 1.82. Found: C, 61.91; H, 6.44; N, 1.80.

The structure assigned to streptoval C is set out in Formula 10.

EXAMPLE VII
PREPARATION OF DES-O-METHYL STREPTOVAL C

A mixture of 770 mg. of streptovaricin C in 50 ml. of t-butyl alcohol and 4.28 g. (20 mmol.) of sodium periodate in 50 ml. of water was stirred in an ice-water bath for 30 minutes, and then allowed to stand at room temperature for 20 hours. The reaction mixture was diluted with 200 ml. of water and extracted with ethyl acetate three times (500 ml.), and the extract was washed with water and then saline solution and dried over anhydrous sodium sulfate overnight. The dried solution was then evaporated to dryness in vacuo, giving a red oil substance, the principal component of which was streptoval C. The oil was chromatographed over silica gel with 3% methanol in chloroform. Fractions, collected by using a fraction collector, which showed a similar condition on thin layer chromatography (developed with 4% methanol in chloroform) were combined, evaporated to dryness in vacuo. The residue containing des-O-methyl streptoval C was dissolved in a small amount of 1-chlorobutane and precipitated with n-hexane. The solid was formed on standing was filtered and yielded 100 mg. of orange powder. The material analyzed as follows:

M.P. 158°-160° C;

IR (KBr) 3400, 2964, 2927, 1760, 1725, 1682, 1618, 1590, 1528, 1490, 1434, 1362, 1330, 1266, 1187, 800 cm⁻¹;

Analysis: Calculated for $C_{39}H_{45}NO_{14}$: C, 62.31; H, 6.03; N, 1.86; Found: C, 62.65; H, 6.35; N, 2.16.

The structure assigned to des-O-methyl streptoval C is set out in Formula 10.

FORMULA 10

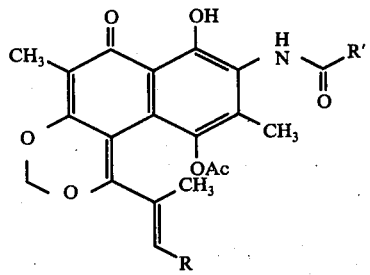

(A) STREPTOVAL C, WHEREIN:

R is 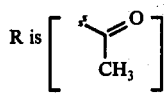

and R¹ is 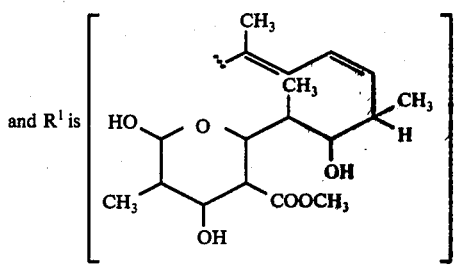

(B) DES-O-METHYL STREPTOVAL C, WHEREIN:

R is 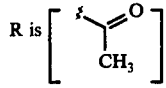

and R¹ is 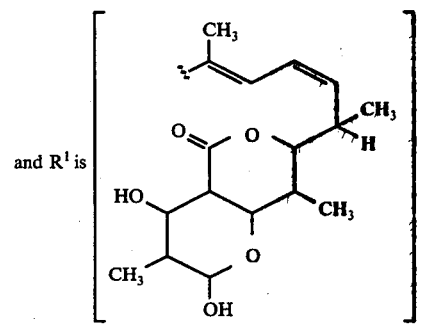

(C) DES-O-METHYL STREPTOVAL C DIACETATE, WHEREIN:

R is 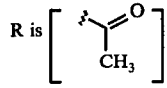

and R¹ is 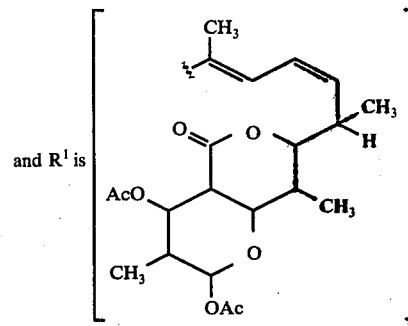

EXAMPLE VIII
PREPARATION OF STREPTOVAL E

A solution of 275 mg. (1.28 mmol.) of sodium periodate in 8 ml. of water was added with stirring to a solution of 100 mg. (0.13 mmol.) of streptovaricin E in 8 ml. of t-butyl alcohol. The reaction flask was wrapped with aluminum foil and kept at room temperature. After 4.5 hours, the reaction mixture was poured into 100 ml. of water and then extracted with three 50-ml. portions of ethyl acetate. The combined organic extracts were dried over magnesium sulfate, filtered, and taken to dryness in vacuo to yield 110 mg. of deep reddish-orange glass. This material was purified by chromatographing it over 15 g. of silica gel, eluting with chloroform/methanol (98/2: v/v). Those fractions containing streptoval E were combined to yield 85 mg. (85%) of pure streptoval E. A rust colored solid was obtained via precipitation from a chloroform solution by the addition of hexane, which solid analyzed as follows:

M.P. 124°–126° C;

UV (ethanol) max 216 (ε22,400), 250 (ε32,200), 262 (sh) (ε31,900), 330 (ε11,300), 450nm (ε10,000);

IR (KBr) 3400, 2921, 1764, 1720, 1660, 1635, 1265, 1192 cm$^{-1}$;

NMR (100 MHz) (CDCl$_3$) δ0.96 (d,3,J=7 Hz, CH-C$\underline{H}_3$), 1.05 (d,3,J=7 Hz, CH-C$\underline{H}_3$), 1.25 (d,3,J=7 Hz, CH-C$\underline{H}_3$), 1.99 (s,3), 2.07 (s,3), 2.17 (s,3), 2.18 (s,3), 2.21 (s,3), 2.26 (s,3), 2.64 (t,1,J=10.5 Hz, C$\underline{H}$-CO$_2$CH$_3$), 2.96 (q,1,J=7 Hz, —CO-C$\underline{H}$-CH$_3$), 3.73 (s,3,CO$_2$C$\underline{H}_3$), 4.08 (d of q, 1, J=7 and 10 Hz, C=CH-C$\underline{H}$-CH$_3$), 4.2–4.5 (m,2), 5.07 (bs,1,O-C$\underline{H}$-OH), 5.3 (very bs,1, O-C$\underline{H}$-O), 5.6–6.0 (very bs,1,O-C$\underline{H}$-O), 5.79 (t,1,J=10 Hz, CH=C$\underline{H}$-CH), 6.49 (t,1, J=11 Hz, C$\underline{H}$=CHCH), 6.59 (q,1,J=1 Hz, C$\underline{H}$=C-CH$_3$), 7.46 (d,1,J=11 Hz, C=C$\underline{H}$CH=), 7.93 (s,1,N$\underline{H}$-CO), 14.23 (s,1,C=C-O$\underline{H}$);

Mass Spec. (70 eV) m/e (relative intensity) 687 (M-78) (1.5), 669 (Z.1), 645 (1.2), 627 (1.5), 460 (3.9), 432 (23), 390 (23), 366 (52), 339 (98), 324 (70), 323 (27), 322 (20), 297 (100), 269 (28), 189 (9), 153 (23), 123 (13), 122 (12), 121 (13), 95 (13);

Analysis: Calculated for $C_{40}H_{47}NO_{14}$: C, 62.73; H, 6.18; N, 1.83; Found: C, 62.20; H, 6.19; N, 1.92.

The structure assigned to streptoval E is set out in Formula 11.

FORMULA 11

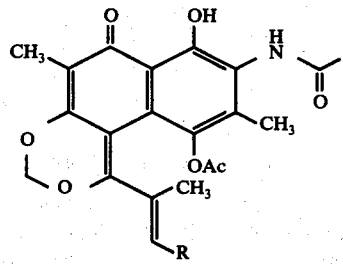

(A) STREPTOVAL E, WHEREIN:

R is [structure with CH$_3$];

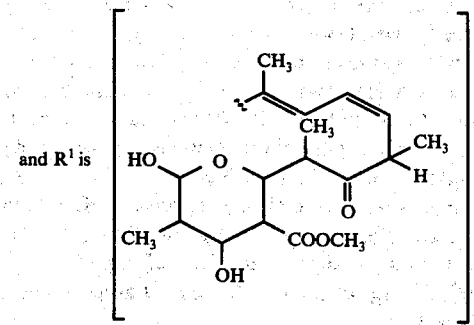

and R$^1$ is (B) STREPTOVAL E DIACETATE-A, WHEREIN

R is [structure with CH$_3$];

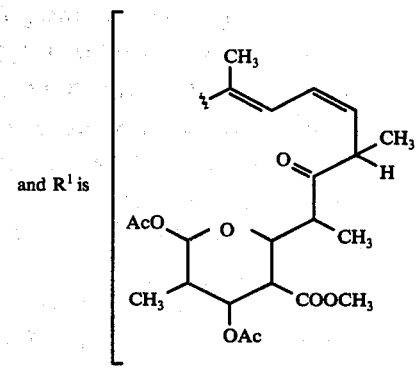

and R$^1$ is (C) STREPTOVAL E DIACETATE-B, WHEREIN:

R is [structure with CH$_3$];

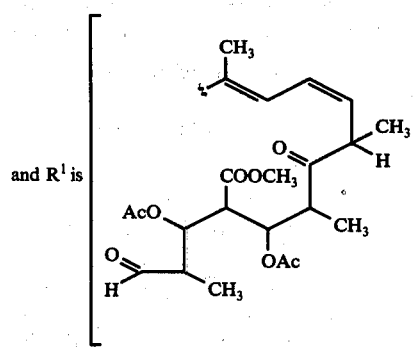

and R$^1$ is

EXAMPLE IX

PREPARATION OF STREPTOVAL F

A solution containing 151 mg. (0.200 mmol.) of streptovaricin F (Formula 2), 66 mg. (0.298 mmol.) of sodium periodate, 7 ml. of ethanol, and 7 ml. of water was magnetically stirred at room temperature. The reaction flask was wrapped with aluminum foil. After 21 hours, the reaction was stopped, and most of the ethanol was removed in vacuo. The residual aqueous solution was diluted with 15 ml. of water and extracted with two 221-ml. portions of ethyl acetate. The organic extracts were combined, dried over magnesium sulfate and filtered. The filtrate was taken to dryness in vacuo, and the residue was chromatographed over 50 g. of silica gel eluting with chloroform/methanol (97/3: v/v). Fractions rich in streptoval F were combined to yield 118 mg. of a red-orange glass. The residue was further purified via preparative tlc of two 20×20 cm. plates (1 mm, PF 254 silica gel). Each plate was developed three times in benzene/acetone (4/1: v/v). The major red-orange band corresponding to streptoval F was mechanically removed, eluted with ethyl acetate/ethanol (1/1: v/v) and filtered. The filtrate was taken to dryness in vacuo to yield 86 mg. of streptoval F as a red-orange glass, which analyzed as follows:

M.P. 167°–170° C;

UV (ethanol) 211 (ε21,500), 252 (ε31,600), 263 (sh) (ε28,800), 333 (ε8,300), 450nm (ε8,900);

IR (KBr) 3430, 2970, 2930, 1760, 1725, 1685, 1620, 1590, 1365, 1335, 1270, 1195 cm$^{-1}$;

Mass Spec. (70 eV) m/e (relative intensity) 655 (M-96) (0.2), 637 (1), 629 (2.2), 619 (0.6), 614 (1.4), 613 (2), 612 (1.2), 611 (2.2), 475 (10), 434 (23), 433 (15), 432 (22), 416 (17), 414 (12), 390 (17), 366 (27), 350 (15), 348 (10), 339 (60), 324 (58), 323 (37), 322 (31), 321 (24), 308 (16), 307 (12), 306 (12), 297 (100), 269 (28), 155 (20), 153 (19), 109 (52);

NMR (CDCl$_3$) 0.97 (d,3,J=7 Hz, CH-CH$_3$), 1.13 (d,3,J=7 Hz, CH-CH$_3$), 1.43 (s,3), 1.98 (s,3), 2.04 (s,6), 2.15 (s,3), 2.18 (s,3), 2.26 (s,3), 2.4-2.8 (m,1), 4.03 (d,1,J=2 Hz), 4.2-4.6 (m,2), 5.08 (bs,1), 5.1-5.4 (very bs,1), 5.77 (d,1,J=11 Hz, CH=CH), 5,5-5.9 (very bs,1), 6.45 (t,1,J=11 Hz, =CHCH=CH), 6.62 (s,1, C=CH), 7.95 (d,1,J=11 Hz, C=CH-CH=), 8.18 (s,1,CO-NH), 14.17 (s,1,C=C-OH);

Analysis: Calculated for C$_{39}$H$_{45}$NO$_{14}$: C, 62.31; H, 6.03; N, 1.86 Found: C, 60.96; H, 6.44; N, 2.10.

The structure assigned to streptoval F is set out in Formula 12.

FORMULA 12

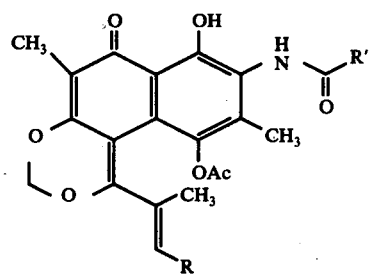

(A) STREPTOVAL F,

WHERE IN: R is $\begin{bmatrix} \text{\Large \ensuremath{\diagup}}\!\!\!\!\!\!\text{C=O} \\ \text{CH}_3 \end{bmatrix}$ ;

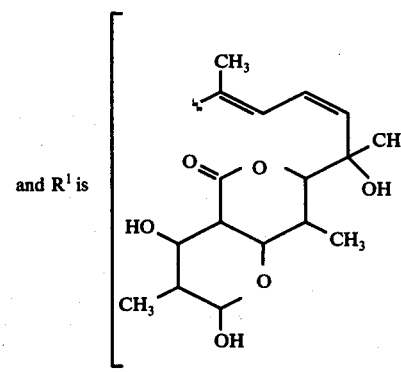

(B) STREPTOVAL F, DIACETATE-A

WHEREIN: R is $\begin{bmatrix} \text{\Large \ensuremath{\diagup}}\!\!\!\!\!\!\text{C=O} \\ \text{CH}_3 \end{bmatrix}$ ;

and R$^1$ is 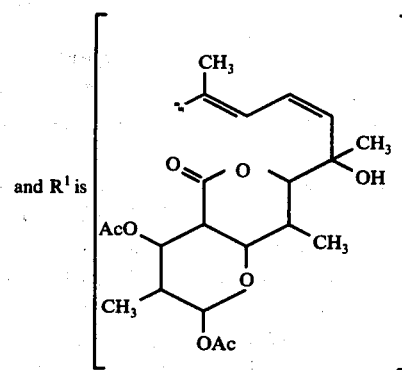

(C) STREPTOVAL F, DIACETATE-B

WHEREIN: R is $\begin{bmatrix} \text{\Large \ensuremath{\diagup}}\!\!\!\!\!\!\text{C=O} \\ \text{CH}_3 \end{bmatrix}$ ;

and R$^1$ is 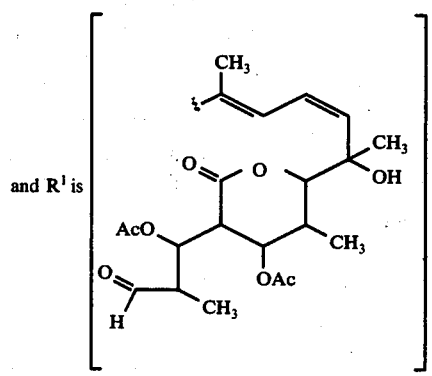

EXAMPLE X

PREPARATION OF ISOSTREPTOVAL G

A solution containing 208 mg. (0.265 mmol.) of streptovaricin G, 60 mg. (0.28 mmol.) of sodium periodate, 10 ml. of ethanol, and 8 ml. of water was magnetically stirred at room temperature. The reaction flask was wrapped with aluminum foil. After 6.5 hours the reaction was stopped and most of the ethanol was removed in vacuo. The aqueous solution was diluted with 15 ml. of water and was then extracted with three 25-ml. portions of ethyl acetate. The organic extracts were combined, dried (over magnesium sulfate), and filtered. The filtrate was taken to dryness in vacuo to yield 217 mg. of a red-orange glass. The residue was purified via preparative tlc using three 20×20 cm. plates (1 mm. thickness, PF254 silica gel). Each plate was developed twice in chloroform/methanol (95/5: v/v). The four major zones were mechanically removed, eluted with ethyl acetate/ethanol (1/1: v/v) and filtered. The filtrates were taken to dryness to yield: 27 mg. of zone 1 (highest Rf); 27 mg. of zone 2; 65 mg. of zone 3; and 2 mg. of zone 4.

Zone 1 was crystallized from methylene chlorideether to yield 25 mg. of prestreptovarone (M.P. 180°–182° C).

Zone 2 was identified as starting material by mens of its mass spectrum.

Zone 3 was the desired isostreptoval G; it was lyophilized from benzene to yield an orange-colored amorphous solid which was analyzed as follows:

M.P. 139°-143° C;

UV (ethanol) 210 (ε29,100), 243 (ε39,200), 287 (ε32,900), 332 (sh) (ε16,000), 436nm (ε14,900);

IR (KBr) 3440, 2980, 2940, 1750 (very broad), 1680, 1615, 1600, 1340, 1270, 1195 cm$^{-1}$;

Mass Spec. (70 eV) m/e (relative intensity) 783 (M+)(0.15), 765 (0.1), 747 (0.1), 695 (0.3), 494 (2.2), 438 (3.7), 434 (3), 433 (5), 432 (7), 390 (30), 297 (6), 269 (7), 199 (19), 197 (15), 185 (8), 183 (9), 182 (8), 181 (15), 179 (11), 171 (11), 169 (13), 165 (17), 155 (17), 153 (44), 151 (30), 149 (36;1 ), 143 (28), 139 (39), 127 (29), 125 (27), 124 (27), 123 (27), 122 (20), 121 (18), 115 (35), 114 (99), 113 (83), 111 (100), 103 (92), 99 (90), 95 (70);

NMR (CDCl$_3$) 0.91 (d,6,J=7 Hz, 2 CH-C$\underline{H}_3$), 1.23 (s,3), 1.96 (s, 3), 2.03 (s,3), 2.17 (s,3), 2.31 (s,9), 2.8-3.1 (m,1), 3.73 (s,3), 4.00 (d of d, 1, J=4 and 10 Hz, O-C$\underline{H}$-), 4.2-4.5 (m,1), 4.97 (d,1,J=2 Hz, O-C$\underline{H}$-), 5.23 (d,1,J=5 Hz), 5.87 (d,1,J=5 Hz, O-C$\underline{H}$-O), 6.01 (bs,1,C=CH), 6.34 (d,1,J=11 Hz, -C$\underline{H}$=CH), 6.85 (t,1,J=11 Hz, =CHC$\underline{H}$=CH), 8.11 (d,1,J=11 Hz, C=C$\underline{H}$-CH=), 8.19 (s,1,CO-N$\underline{H}$-), 14.42 (s,1,C=C-O$\underline{H}$);

Analysis: Calculated for $C_{40}H_{49}NO_{15}$: C, 61.29; H, 6.30; N, 1.79 Found: C, 61.87; H, 6.34; N, 1.92.

The structure assigned to isostreptoval G is set out in Formula 13.

Zone 4 was a mixture of two compounds containing streptoval G (Formula 13).

FORMULA 13

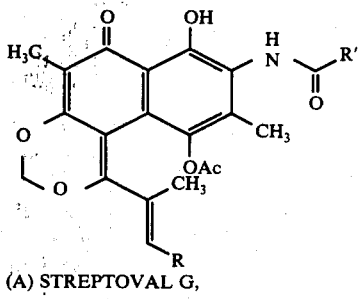

(A) STREPTOVAL G,

WHEREIN: R is [structure with H$_3$C, =O] ; and R$^1$ is

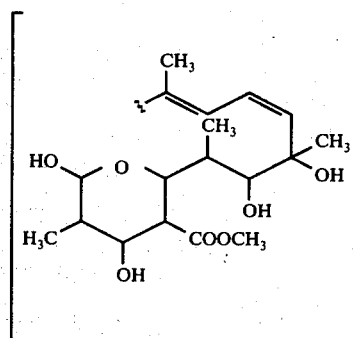

(B) ISOSTREPTOVAL G,

-continued

WHEREIN: R is 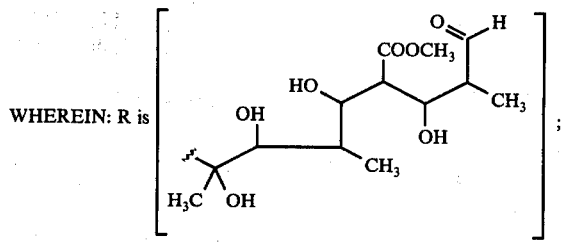

and R$^1$ is 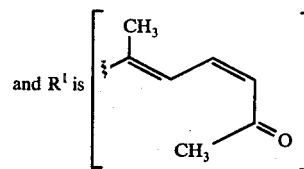

(C) STREPTOVAL J,

WHEREIN: R is [structure with O, CH$_3$];

and R$^1$ is 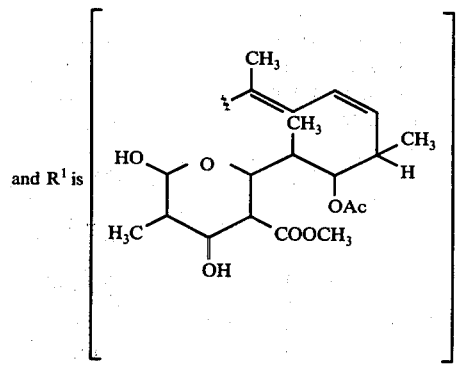

EXAMPLE XI

PREPARATION OF STREPTOVAL J

A solution containing 73 mg. (0.09 mmol.) of streptovaricin J, 59 mg. (0.27 mmol.) of sodium periodate, 4 ml. of ethanol, and 4 ml. of water was magnetically stirred at room temperature. The reaction flask was wrapped with aluminum foil. After 7 hours the reaction was stopped, and most of the ethanol was removed in vacuo. The aqueous solution was diluted with 20 ml. of water and extracted with two 20-ml. portions of ethyl acetate. The organic extracts were combined, dried (MgSO$_4$) and filtered. The filtrate was taken to dryness in vacuo. The resulting residue was purified via preparative thin layer chromatography on a 20X20 cm. plate (1 mm., PF254 silica gel). The plate was developed six times in chloroform/methanol (98/2: v/v). The major red-orange band, corresponding to streptoval J, was mecahanically removed, eluted with ethyl acetate, and filtered. The filtrate was taken to dryness in vacuo to yield 50 mg. of a red-orange glass which was shown to be composed of two closely related materials by nmr and thin layer chromatography [Eastman Chromagram silica gel sheet, chloroform/acetone (4/1: v/v)]. This material was lyophilized from benzene to yield streptoval J as an orange amorphous solid which analyzed as follows:

M.P. 137°-142° C;

UV (ethanol) 213 (ε21,000), 257 (broad) (ε31,300), 330 (ε10,000), 451nm (ε9,600);

IR (KBr) 3420, 3030, 2965, 2930, 1765, 1725, 1680, 1620, 1535, 1490, 1435, 1365, 1335, 1240, 1195, 1135, 1095, 1040, 1010 cm$^{-1}$;

Mass Spectrum (70 eV) m/e (rel intensity) 731 (M-78) (0.15), 727 (0.2), 713 (2.5), 685 (1), 671 (1.2), 627 (0.8), 612 (0.9), 594 (0.8), 489 (0.8), 484 (0.9), 472 (1), 432 (10), 390 (18), 382 (7), 381 (29), 366 (15), 364 (11), 363 (33), 350 (8), 349 (12), 348 (44), 340 (23), 339 (63), 338 (33), 337 (12), 325 (16), 324 (67), 323 (19), 322 (43), 321 (66), 320 (25), 303 (16), 300 (14), 298 (41), 297 (100), 296 (45), 283 (9), 282 (9), 272 (11), 271 (10), 270 (9), 269 (37), 257 (8), 256 (8), 255 (10), 254 (15), 253 (11), 243 (12), 241 (11), 239 (14), 227 (15), 225 (13), 223 (8), 219 (8), 218 (7), 217 (19), 215 (10), 211 (17), 197 (13), 187 (11), 185 (18), 183 (10), 181 (9), 180 (11), 179 (14), 175 (12), 173 (8), 171 (17), 167 (9), 166 (9), 165 (24), 161 (12), 159 (27), 157 (15), 153 (29), 152 (15), 151 (15), 150 (18), 149 (12), 145 (11), 143 (9), 139 (10), 135 (9), 133 (21), 129 (13), 128 (10), 127 (10), 123 (12), 122 (34), 121 (10), 119 (12), 115 (11), 114 (7), 111 (11), 109 (10), 107 (14), 106 (10), 105 (22), 95 (19), 93 (17), 91 (25), 83 (7), 82 (8), 81 (6), 79 (17), 77 (16), 69 (26), 67 (14), 65 (13), 60 (26), 59 (12), 55 (17), 45 (32), 44 (63), 43 (65), 41 (17), 39 (9);

Analysis: Calculated for $C_{42}H_{51}NO_{15}$: C, 62.27; H, 6.35; N, 1.73. Found: C, 61.78; H, 6.42; N, 1.92.

The structure assigned to streptoval J is set out in Formula 13.

EXAMPLE XII

PREPARATION OF ACYLATED STREPTOVAL DERIVATIVES

A. Preparation of Streptoval C Triacetate-A

To a cooled solution of 950 mg. of streptoval C in 10 ml. of pyridine was added 50 ml. of acetic anhydride with stirring. The mixture was stirred in an ice-water bath for 15 minutes and allowed to stand at room temperature overnight. Thereafter the reaction mixture was bathed in ice-water and 100 ml. of ethanol was added dropwise to decompose the excess of acetic anhydride. After it had been stirred in an ice-water bath for one hour, the mixture was evaporated to a small volume under reduced pressure, the concentrate was diluted with a large amount of water and repeatedly extracted with ethyl acetate. The combined extract was washed with water and then saline solution and dried over anhydrous sodium sulfate overnight. The dried solution was then evaporated to dryness in vacuo, affording a red oil. The oil was chromatographed over silica gel with 1% methanol in chloroform. The fractions containing streptoval C triacetate-A were combined and dissolved in 1-chlorobutane and n-hexane. The solid which formed on standing was filtered and yielded 653 mg. of an orange powder. The material analyzed as follows:

M.P. 122°-124° C;

IR (KBr) 1765 (sh), 1745, 1690, 1625, 1594, 1240, 1194, 800 cm$^{-1}$;

UV (methanol) max 210, 247, 325 and 443 nm.

The structure assigned to streptoval C triacetate-A is set out in Formula 9 and is identical to that of streptoval B diacetate-A and streptoval J diacetate-A.

B. Preparation of Streptoval C Triacetate-B

To a solution of 554 mg. of streptovaricin C triacetate in 150 ml. of methanol was added 15 g. of sodium periodate in 150 ml. of water with cooling in an ice-water bath. The reaction flask was covered and allowed to stand at room temperature for 48 hours. Thereafter, the reaction mixture was poured into water, and extracted with ethyl acetate three times. The extract was washed with water and then saline solution and dried over anhydrous sodium sulfate overnight. The dried solution was then evaporated to dryness in acuo, giving a red oil which was chromatographed over silica gel with 50% ethyl acetate in benzene. The fractions containing streptoval C triacetate-B were collected and dissolved in 1-chlorobutane. The solid which formed on standing was filtered and yielded 180 mg. of amorphous powder. The material analyzed as follows:

M.P. 100°-102° C;

IR (KBr) 1763 (sh), 1735, 1687, 1623, 1596(sh), 1494, 1441, 1370, 1336, 1237, 1199, 1020 cm$^{-1}$;

UV (methanol) max 210, 258, 330, and 450nm (ε40,950, 50,900, 14,450, 10,700);

Mass Spec. m/e 893, 863, 833, 817, 799, 791, 773, 761, 755, 731, 713, 701, 671, 687, 369, 297, 267.

The structure assigned to streptoval C triacetate-B is set out in Formula 9, and is identical to streptoval B diacetate-B and streptoval J diacetate-B.

C. Preparation of Streptovadienal C

In addition to products such as streptoval C triacetate-B which are formed via cleavage of acylated streptovaricins, the present invention contemplates formation of structurally similar compounds (termed streptovadienals) through cleavage of acylated streptovaricins followed by elimination of acyl groups with consequent unsaturation at the sites of elimination. Thus the product, streptovadienal C, may be prepared according to the following procedure.

A solution of 895 mg. (1.00 mmol.) of streptovaricin C triacetate, 350 mg. (1.63 mmol.) of sodium periodate, 10 ml. of ethanol and 10 ml. of water was stirred at room temperature. The reaction flask was wrapped with aluminum foil. Because solution was not complete after 3 hours, 5 ml. of chloroform was added to the reaction mixture. This resulted in a two phase system which was stirred vigorously.

After 23 hours, thin layer chromatography (GF 254 silica gel, chloroform-methanol (98/2: v/v) indicated very little reaction. At this point an additional 350 mg. (1.63 mmol.) of sodium periodate was added along with 5 ml. of ethanol which resulted in a homogeneous solution. An additional 700 mg. (3.62 mmol.) of sodium periodate was added after 53.5 hours and again after 72 hours. The reaction was stopped after 97.5 hours, and most of the organic solvent was removed in vacuo. The resulting aqueous suspension was diluted with 60 ml. of water and extracted with two 40-ml. portions of ethyl acetate. The extracts were combined, dried over magnesium sulfate and filtered. The filtrate was taken to dryness in vacuo, and the residue was chromatographed over 200 g. of silica gel eluting with benzene-methanol (96/4: v/v). However, no separation occurred, contrary to the results on thin layer chromatography. All the material was washed off the column with benzene-methanol (88/12: v/v).

The material from the first column was chromatographed over 200 g. of silica gel eluting with 100 ml. of chloroform followed by chloroform-methanol (99/1: v/v) until elution was complete. No fractions were collected until colored material began to elute and then 7-8 ml. fractions were collected. Fraction nos. 2-20 contained predominantly streptovadienal C and were combined to yield 615 mg. of crude streptovadienal C.

Fraction nos. 45–55 contained predominantly unreacted starting material; these fractions were combined and crystallized from methylene chloride-ether to yield 46 mg. of streptovaricin C triacetate as orange needles.

The 615 mg. of crude streptovadienal C was chromatographed over 70 g. of silica gel eluting with chloroform-ethyl acetate (95/5: v/v). No fractions were collected until colored material began to elute and then 7–8 ml. fractions were collected. Fractions 11–23 contained pure streptovadienal C and were combined to yield 302 mg. (39%) of the desired material as a red-orange glass. A portion of this material was lyophilized from benzene to give a red-orange amorphous solid which analyzed as follows:

M.P. 108°–112° C;

UV (EtOH) 215 (ε26,600), 259 (ε44,500), 331 (ε10,600), 448nm (ε9,300);

IR (KBr) 3420, 3965, 2930, 2870, 2715, 1765, 1725, 1680, 1620, 1590, 1490, 1435, 1365, 1335, 1270, 1235, 1195, 1135, 1090, 1040, 1015, 730 cm$^{-1}$;

NME (100 MHz) (CDCl$_3$) δ1.05 (d,3,J=7 Hz, CH-CH$_3$), 1.11 (d,3,J=7 Hz, CH-CH$_3$), 1.79 (slightly broadened singlet, 3), 2.01 (s,3), 2.07 (s,3), 2.09 (s,3), 2.15 (slightly broadened singlet,3), 2.19 (slightly broadened singlet,3), 2.22 (s,3), 2.28 (s,3), 3.09 (m,1,J=6, 7 and 10.5 Hz, CH-CH$_3$), 3.43 (m,1,J=5.5, 7 and 10.5 Hz, CH-CH$_3$), 3.87 (s,3,CO$_2$CH$_3$), 4.97 (d of d,1,J=5.5 and 6 Hz, CH-OAc), 5.1-5.5 (bs,1,0-CH-O), 5.6-6.0 (bs,1,0-CH-O), 5.75 (d of d,1,J=10.5 and 11 Hz, CH=CH-CH), 6.35 (d,1,J= 10.5 Hz, C=CH-CH), 6.44 (t,1,J=11 Hz, CH=CHCH), 6.62 (q,1,J=1.2 Hz, CH=C-CH$_3$), 6.97 (q,1, J=1.2 Hz, CH=C-CH$_3$), 7.41 (d,1,J= 11 Hz, C=CH-CH=), 7.72 (s,1,NHCO), 9.40 (s,1, —CH=O), 14.26 (s,1,C=C-OH);

Mass Spec. (70 eV) m/e (rel intensity) 713 (M-130) (19), 701 (17), 671 (14), 653 (7), 642 (10), 627 (9), 584 (11), 462 (11), 448 (10), 421 (10), 420 (21), 405 (11), 402 (10), 399 (10), 396 (21), 395 (17), 390 (17), 381 (20), 369 (99), 363 (100), 369 (4.8), 363 (5.2), 348 (7), 339 (7), 324 (4), 322 (6), 321 (20), 320 (8), 297 (14), 271 (6), 253 (5), 243 (7), 225 (9), 185 (5), 171 (5), 165 (9), 159 (7), 153 (5), 133 (7), 128 (5), 105 (11), 91 (11), 77 (9), 69 (12), 67 (10), 60 (15), 55 (11), 45 (20), 44 (28), 43 (88), 41 (18), 28 (100);

Analysis: Calculated for C$_{42}$H$_{47}$NO$_{13}$: C, 65.19; H, 6.12; N, 1.81. Found: C, 64.67; H, 6.14; N, 1.96.

The structure assigned to streptovadienal C is set out in Formula 14.

FORMULA 14

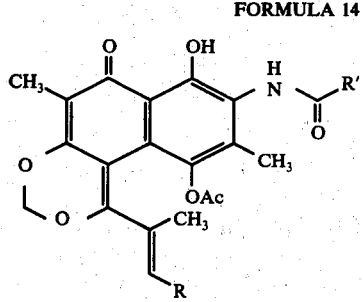

(A) STREPTOVADIENAL A

WHEREIN: R is $\left[ \begin{array}{c} \text{O} \\ \diagup\!\!\diagdown \\ \text{CH}_3 \end{array} \right]$ ;

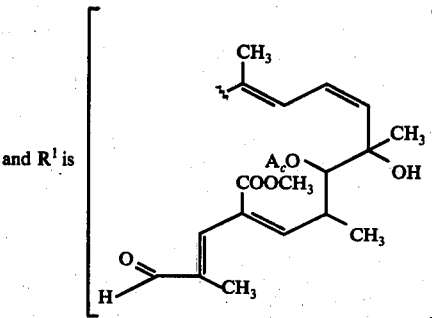

(B) STREPTOVADIENAL C

WHEREIN: R is $\left[ \begin{array}{c} \text{O} \\ \diagup\!\!\diagdown \\ \text{CH}_3 \end{array} \right]$

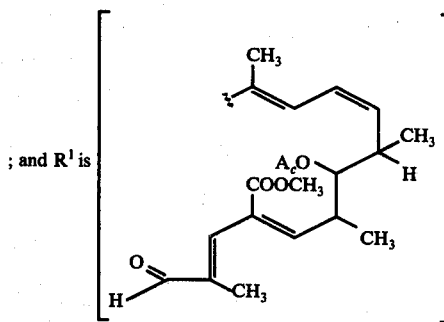

(C) STREPTOVADIENAL F

WHEREIN: R is $\left[ \begin{array}{c} \text{O} \\ \diagup\!\!\diagdown \\ \text{CH}_3 \end{array} \right]$

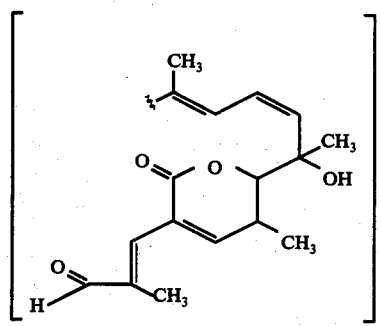

(D) STREPTOVADIENAL E

WHEREIN: R is $\left[ \begin{array}{c} \text{O} \\ \diagup\!\!\diagdown \\ \text{CH}_3 \end{array} \right]$

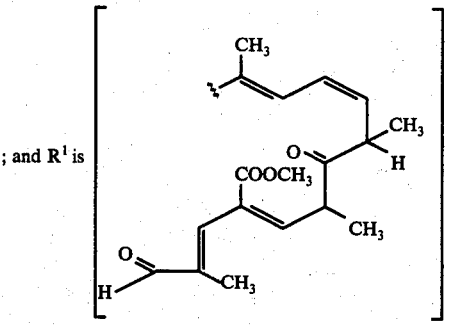

Other acylated streptovals of the present invention may be prepared by the procedures set out above for the preparation of streptoval C triacetate-A and streptoval C triacetate-B and streptovadienal C.

Thus, streptoval A diacetate-A (Formula 7) is prepared by the two mole acetylation of streptoval A. Streptoval A diacetate-B )Formula 7) is prepared by the two mole acetylation of streptovaricin A, followed by periodate cleavage. It will be noted that streptoval G triacetate-A, prepared by three mole acetylation of streptoval G, is identical to streptoval A diacetate-A. Similarly, streptoval G triacetate-B, prepared by three mole acetylation of streptovaricin G followed by periodate cleavage, is identical to streptoval A diacetate-B.

Streptoval C triacetate-A, as shown in Example XII (A), is prepared by three mole acetylation of streptoval C and is identical to streptoval J diacetate-A — the product of a two mole acetylation of streptoval J. Streptoval C triacetate-B, as shown in Example XII (B), is prepared by three mole acetylation of streptovaricin C followed by periodate cleavage and is identical to streptoval J diacetate-B — the product of two mole acetylation of streptovaricin J followed by periodate cleavage.

Des-O-methyl streptoval C diacetate (Formula 10) may be prepared by two mole acetylation of des-O-methyl streptoval C.

Streptoval E diacetate-A (Formula 11) may be prepared by two mole acetylation of streptoval E and streptoval E diacetate-B (Formula 11) may be prepared by two mole acetylation of streptovaricin E followed by periodate cleavage.

Streptoval F diacetate-A (Formula 12) may be prepared by three mole acetylation of streptoval F and streptoval F diacetate-B (Formula 12) may be prepared by three mole acetylation of streptovaricin F followed by periodate cleavage.

As previously noted, streptoval G triacetate-A and streptoval G triacetate-B are respectively identical to streptoval A diacetate-A and streptoval A diacetate-B.

Isostreptoval G diacetate (Formula 8) is identical to isostreptoval A monoacetate. Isostreptoval G triacetate is identical to isostreptoval A diacetate.

Preparation of streptovadienals G, F and E (Formula 14) may be prepared according to the procedures of Example XII (C) through respective use of streptovaricin G triacetate, streptovaricin F diacetate and streptovaricin E diacetate as starting materials.

Tables A-G below respectively set forth activities of representative products of the invention relative to streptovaricin C in the following assays: (A) reverse transcriptase (RNA-directed DNA polymerase); (B) DNA-directed DNA polymerase; (C) L 1210 three-day cytotoxicity; (D) AKR growth inhibition; (E) bacterial RNA polymerase; (F) B. subtilis bacterial inhibition; and, (G) S. lutea bacterial inhibition.

The assay and work-up conditions for reverse transcriptase analysis were essentially those described by Brockman, et al., (Nature, 230, 249 (1971)), except for eliminating the phosphate from the washing solution (10% trichloroacetic acid).

The assay and work-up conditions for DNA polymerase were essentially those described by Magee (Virology, 17, 604 (1962)). The reaction mixture contained (in moles): potassium phosphate (pH 7.4), 15; EDTA, 2; ATP, 0.05; $Mg^{++}$, 2.5; triphosphates of CdR, deoxyguanosine, and AdR, 0.01 each; TdR triphosphate-$^3$H, 0.01 (100 mCi/mmol.); DNase-treated E. coli DNA, 0.2 mg.; and cell sonicate, 0.2 mg. protein in a total volume of 0.5 ml. After incubation at 37° C for up to 60 minutes with continual gentle shaking, the reactions were stopped by the addition of carrier DNA (200 g.) and PCA (to 0.5 N) containing 2% Celite. The pellet was washed with PCA, dissolved in 1 N NaOH, reprecipitated and washed with PCA, extracted with 0.15 ml. 0.5 N PCA (70°) for 20 minutes, and counted in 12 ml. of Diotol.

The assay for three-day L1210 cytoxicity analysis was according to the procedure of Buskirk (Proc. Tissue Culture Assoc., 20, 23 (1969)). The 50% and 90% inhibitory doses were determined by incubating 5 ml. of L1210 cells in culture ($5 \times 10^3$ cells/ml.) with drug of different concentrations at 37° C for 3 days. Cell growth was determined with a Coulter counter.

The assay for inhibition of AKR cells in culture was as follows. Four ml. of cells (ca. $1 \times 10^4$ cells/ml.) were pipetted into sterilized plastic culture tubes with screw caps ($16 \times 125$ mm.; Falcon Plastics, Oxnard, California). The experiment was initiated by adding 1.0 ml. of medium or drug at different concentrations and incubating at 37° C for 3 days. Cell growth was determined twice a day for 3 days. The percent inhibition was calculated from the controls (no drug).

The assay for bacterial RNA polymerase followed the procedure of Reusser (J. Bacterial., 105, 580 (1971)). Assay mixtures were prepared containing in a total volume of 0.25 ml.: Tris-hydrochloride buffer, pH 7.9, 5 μmoles; $MgCl_2$, 1 μmole; mercaptoethanol, 3 μmoles; $MnCl_2$, 0.25 μmole; guanosine triphosphate, cytidine triphosphate, uridine triphosphate, 0.1 μmole each; adenosine triphosphate 8-14C, 0.1 μmole containing 0.05 μCi; dAT, 0.2 units; polymerase, ~35 μg. The reaction mixtures were incubated at 30° C for 15 min.

The assay for B. subtilis bacterial inhibition was obtained on plates with B. subtilis UC 564 spores in agar with the following composition per liter:

| | |
|---|---|
| $Na_2HPO_4 \cdot 7H_2O$ | 1.7 gm |
| $KH_2PO_4$ | 2.0 gm |
| $MgSO_4$ | 0.1 gm |
| $(NH_4)_2SO_4$ | 1.0 gm |
| Agar | 15 gm |

After autoclaving, 10 ml. of 20% glucose was added. The seeding rate was approximately $10^9$ spores per liter. Test solutions were applied to ½-inch paper discs (Schleicher & Schuell 740E) with 0.08 ml. per disc.

The assay for S. lutea inhibition was as follows. Water-soluble preparations were dissolved in brain heart infusion broth (Difco) to 1 mg./ml. Water-insoluble preparations were dissolved (or suspended) in dimethylformamide to 10 mg./ml. and diluted with brain heart broth to 1 mg./ml. Two-fold serial dilutions were made with broth starting with 1 mg./ml. with final volumes of 01. ml. per dilution. Overnight bacterial cultures were diluted 1:20,000 with brain heart and 0.1 ml. of diluted culture was added to each dilution of antibiotic (final total volume was 0.2 ml.). This was all done in plastic microtest plates (Microtest II Tissue Culture Plate, Bioquest). The plates were incubated at 37° for 16-18 hours and the minimum inhibitory concentrations (MIC) were recorded as the smallest concentration in which no visible growth occurred.

TABLE A

| REVERSE TRANSCRIPTASE | |
|---|---|
| COMPOUND | % INHIBITION |
| Streptovaricin C | 47.9 |
| Prestreptovarone | 60.1 |
| Streptovarone | 59.4 |

TABLE A-continued

REVERSE TRANSCRIPTASE

| COMPOUND | % INHIBITION |
| --- | --- |
| Streptovaricin A Triacetate | 76.0 |
| Streptovaricin C Triacetate | 79.0 |
| Streptovaricin C Tetra-acetate | 80.0 |
| Streptoval A | 100.0 |
| Isostreptoval A | 7.8 |
| Streptoval B | 99.0 |
| Streptoval C | 84.0 |
| Des-O-methyl Streptoval C | 54.4 |
| Streptoval E | 95.7 |
| Streptoval F | 8.3 |
| Streptoval C Triacetate-A | 86.2 |
| Streptoval C Triacetate-B | 97.3 |

TABLE B

DNA DIRECTED DNA POLYMERASE

| COMPOUND | % INHIBITION |
| --- | --- |
| Streptovaricin C | 0 |
| Prestreptovarone | 35.4 |
| Streptovarone | 12.2 |
| Streptoval C | 9.2 |

TABLE C

L 1210 CYTOTOXICITY GROWTH

| COMPOUND | (μg./ml.) |
| --- | --- |
| Streptovaricin C | 26–49.0 |
| Streptovarone | 4.6 |
| Isostreptoval A | 13.5 |
| Streptoval C | 7.5 |

TABLE D

AKR CELLS

| COMPOUND | % INHIBITION |
| --- | --- |
| Streptovaricin C | 8.9 |
| Streptovarone | 0.4 |
| Isostreptoval A | 10.7 |
| Streptoval C | 2.1 |

TABLE E

E. COLI RNA POLYMERASE

| COMPOUND | % INHIBITION* |
| --- | --- |
| Streptovaricin C | 66 |
| Prestreptovarone | 0 |
| Streptovarone | 0 |
| Streptoval A | 35 |
| Isostreptoval A | 21 |
| Des-O-methyl Streptoval C | 27 |
| Isostreptoval G | 52 |
| Streptoval E | 7 |

*All concentrations 0.1 μmole/ml. except 0.2 μmole/ml. for Streptoval C, and 0.01 μmole/ml. for Streptovaricin C.

TABLE F

B. SUBTILIS INHIBITION

| COMPOUND | ZONE (mm.) INHIBITION** |
| --- | --- |
| Streptovaricin C | 22 |
| Streptovarone | 0 |
| Streptoval A | 17 |
| Isostreptoval A | 16 |
| Streptoval C | 0 |
| Streptoval E | 0 |

**0.25 μmole/ml. concentration.

TABLE G

S. LUTEA INHIBITION

| COMPOUND | M.I.C. |
| --- | --- |
| Streptoval A | 80 μg/ml |
| Isostreptoval A | 80 μg/ml |

TABLE G-continued

S. LUTEA INHIBITION

| COMPOUND | M.I.C. |
| --- | --- |
| Streptoval E | 75 μg/ml |

*All concentrations 0.1 μmole/ml. except 0.2 μmole/ml. for Streptoval C, and 0.01 μmole/ml. for Streptovaricin C.
**0.25 μmole/ml. concentration.

Pharmaceutical compositions of the present invention comprise a minor proportion of one of the above compounds and a major proportion of a carrier or diluent. The nature of the composition and the carrier or diluent will, of course, depend on the desired route of administration, i.e., orally or parenterally.

Thus, for example, antibacterial pharmaceutical compositions could be prepared in the form of compressed tablets, effervescent tablets, powders, granules, capsules, aqueous solution suspensions in edible oils, aqueous solutions or other dosage forms which are particularly useful for oral administration. Similarly, liquid preparations or formulations may be employed for parenteral use in a medium including a sterile solvent or a sterile suspending vehicle containing an injectable oil, or water-containing hydrophilic colloids such as sodium carboxymethyl cellulose, methyl cellulose, polyvinylpyrrolidone, gelatine, tragacanth and the like.

Antibacterial pharmaceutical compositions might also take the form of topical preparations such as ointments and aerosol sprays. They may also include other compatible therapeutic agents.

In the use of compounds of the present invention for the treatment of localized diseases of viral origin, contact between the compounds and the afflicted area may be accomplished by dissolving the compounds in a suitable solvent, e.g., aqueous DMSO, ethanol, methanol, chloroform, acetone, methylene chloride, and ethyl acetate and introducing the solution directly or indirectly into the environment of the disease site.

The concentration of the compounds in the environment of the disease site may be from 20 mcg./ml. to 400 mcg./ml. with from 20 mcg./ml. to 50 mcg./ml. being preferred.

The amount of the compound to be administered for a given antibacterial or other activity depends on the species, age, and weight of the host as well as the particular conditions to be treated and the route of administration. In general, the parenteral dose expressed as the total amount of the compound is from about 5 to 50 mg/kg. body weight. An oral dose is from about 1 to 10 times the parenteral dose or from 50 to 500 mg./kg. body weight given 1 to 4 times daily.

The following table indicates dosages, for various species (adult):

| Species | Parenteral (mg./kg./day) | Oral (mg./kg./day) |
| --- | --- | --- |
| Dogs | 5 to 50 | 20 to 500 |
| Cats | 5 to 50 | 20 to 500 |
| Rats | 30 to 100 | 100 to 500 |
| Mice | 30 to 100 | 100 to 500 |
| Human | 5 to 100 | 20 to 500 |

The therapeutic methods of the present invention comprise administration of effective amounts of the abovementioned pharmaceutical compositions to a host afflicted with a bacterial or viral disease.

The foregoing detailed description has been given for clearness of understanding only, and no unnecessary limitations should be understood therefrom, as modifications will be obvious to those skilled in the art. For example, it is clear that while only acetylated streptovaricin derivatives have been illustrated other $C_3$ to $C_{18}$ acyl group derivatives such as propionates, butyrates, laurates and the like may be produced.

What is claimed is:

1. A compound of the formula

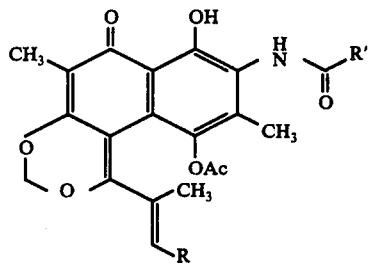

wherein

R IS $\left[\begin{array}{c}\overset{O}{\underset{CH_3}{\|}}\end{array}\right]$; AND R' IS

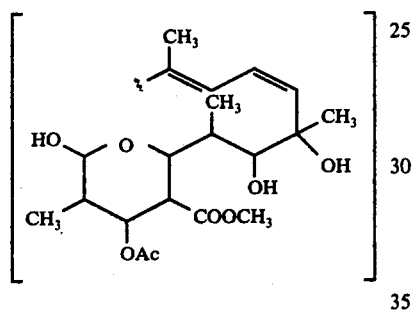

and Ac is an acyl residue of a $C_2$ to $C_{18}$ carboxylic acid.

2. A compound according to claim 1 wherein Ac is an acetyl group.

3. A compound of the formula

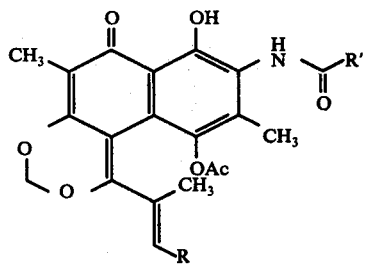

wherein

R IS $\left[\begin{array}{c}\overset{O}{\underset{CH_3}{\|}}\end{array}\right]$;

AND R' IS 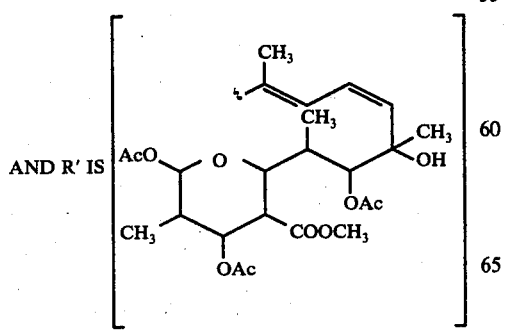

and Ac is an acyl residue of a $C_2$ to $C_{18}$ carboxylic acid.

4. A compound according to claim 3 wherein Ac is an acetyl group.

5. A compound of the formula

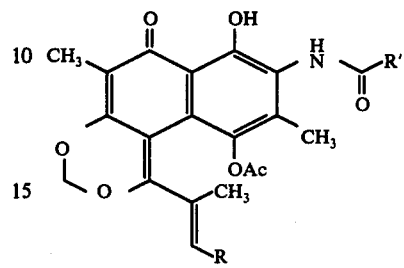

wherein r is $\left[\begin{array}{c}\overset{O}{\underset{CH_3}{\|}}\end{array}\right]$; AND R' is

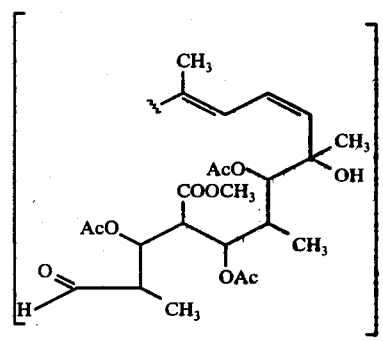

and Ac is an acyl residue of a $C_2$ to $C_{18}$ carboxylic acid.

6. A compound according to claim 5 wherein Ac is an acetyl group.

7. A compound of the formula

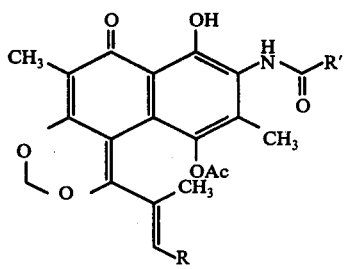

wherein

R IS 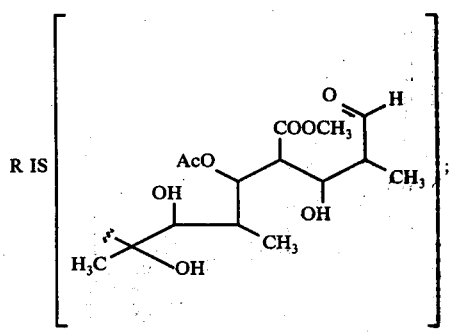

-continued

AND R' IS 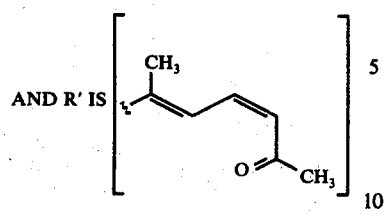

and Ac is an acyl residue of a $C_2$ to $C_{18}$ carboxylic acid.

8. A compound according to claim 7 wherein Ac is an acetyl group.

9. A compound of the formula

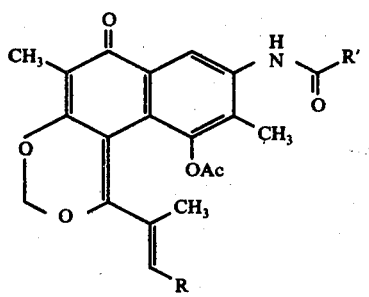

wherein

R IS 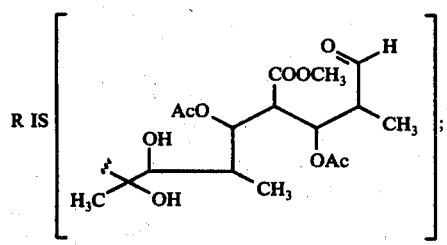;

AND R' IS 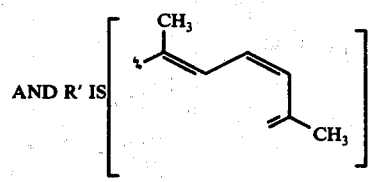

and Ac is an acyl residue of a $C_2$ to $C_{18}$ carboxylic acid.

10. A compound according to claim 9 wherein Ac is an acetyl group.

11. A compound of the formula

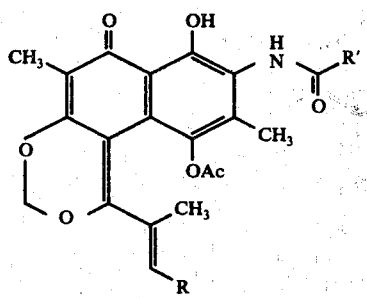

wherein

-continued

R IS 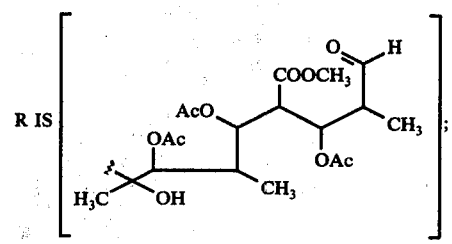;

AND R' IS 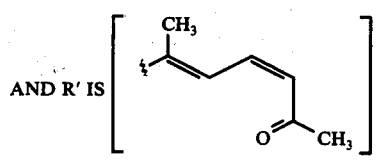

and Ac is an acyl residue of a $C_2$ to $C_{18}$ carboxylic acid.

12. A compound according to claim 11 wherein Ac is an acetyl group.

13. A compound of the formula

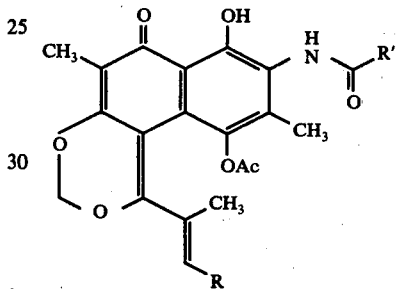

wherein

R IS 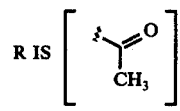;

AND R' IS 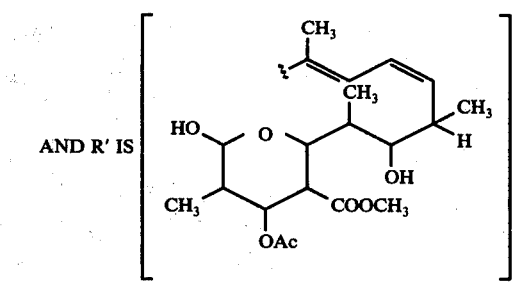

and Ac is an acyl residue of a $C_2$ to $C_{18}$ carboxylic acid.

14. A compound according to claim 13 wherein Ac is an acetyl group.

15. A compound of the formula

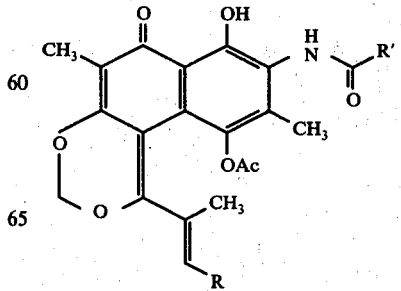

wherein

-continued

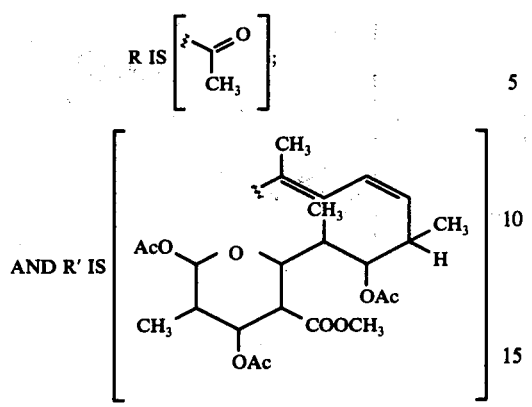

and Ac is an acyl residue of a $C_2$ to $C_{18}$ carboxylic acid.

16. A compound according to claim 15 wherein Ac is an acetyl group.

17. A compound of the formula

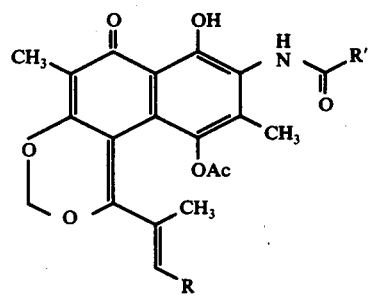

wherein

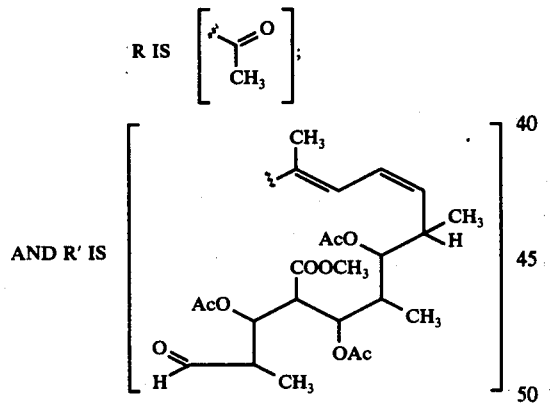

and Ac is an acyl residue of a $C_2$ to $C_{18}$ carboxylic acid.

18. A compound according to claim 17 wherein Ac is an acetyl group.

19. A compound of the formula

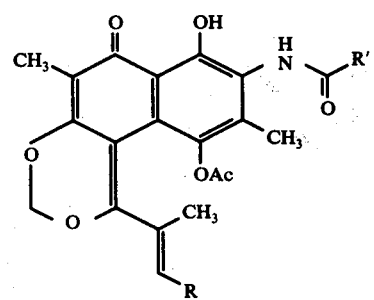

wherein

-continued

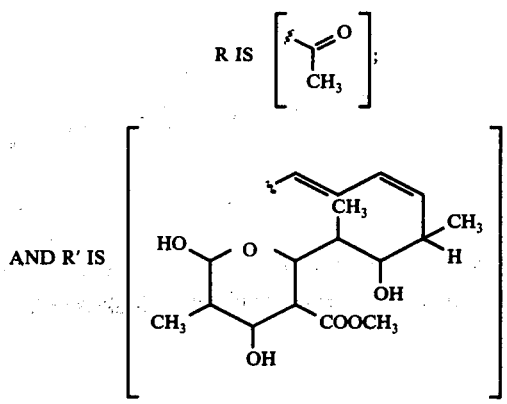

and Ac is an acyl residue of a $C_2$ to $C_{18}$ carboxylic acid.

20. A compound according to claim 19 wherein Ac is an acetyl group.

21. A compound of the formula

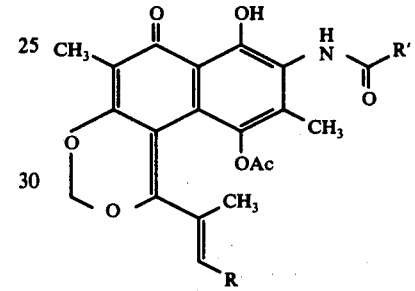

wherein

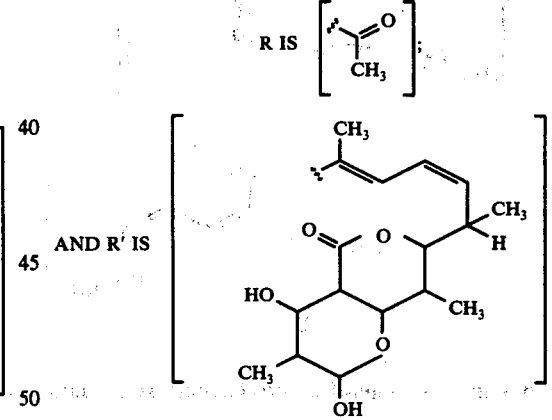

and Ac is an acyl residue of a $C_2$ to $C_{18}$ carboxylic acid.

22. A compound according to claim 21 wherein Ac is an acetyl group.

23. A compound of the formula

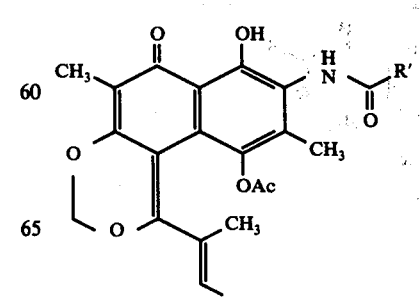

wherein

-continued

R IS [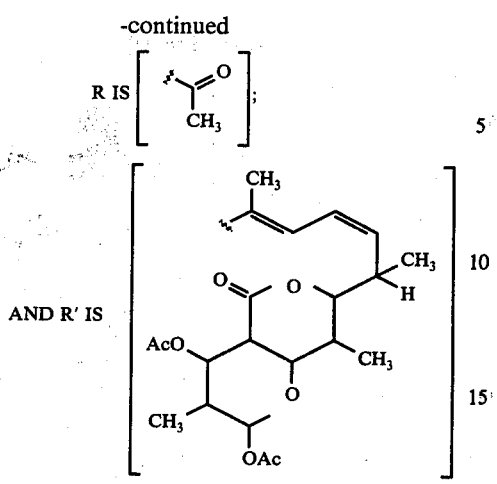

AND R' IS and Ac is an acyl residue of a $C_2$ to $C_{18}$ carboxylic acid.

24. A compound according to claim 23 wherein Ac is an acetyl group.

25. A compound of the formula

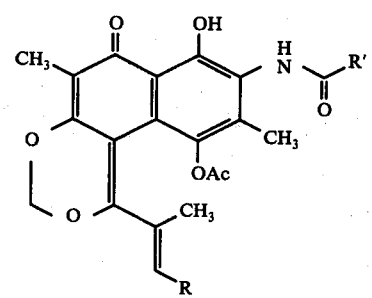

wherein

R IS [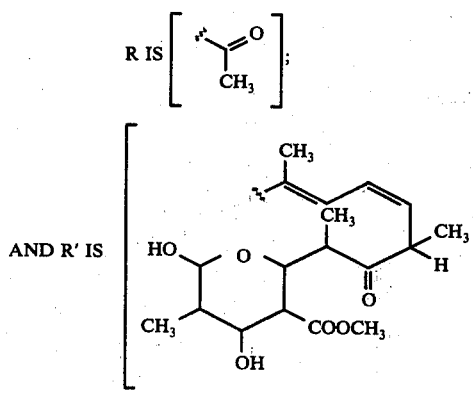

AND R' IS and Ac is an acyl residue of a $C_2$ to $C_{18}$ carboxylic acid.

26. A compound according to claim 25 wherein Ac is an acetyl group.

27. A compound of the formula

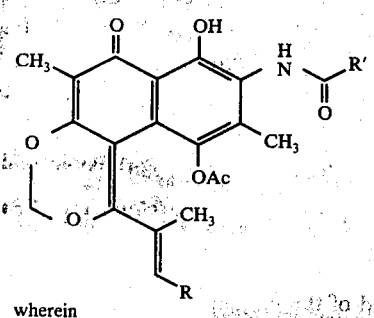

wherein

-continued

R IS [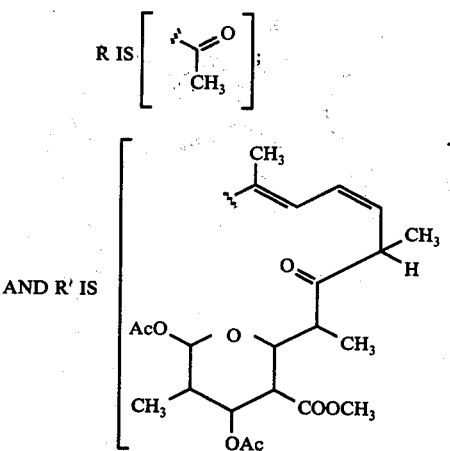

AND R' IS and Ac is an acyl residue of a $C_2$ to $C_{18}$ carboxylic acid.

28. A compound according to claim 27 wherein Ac is an acetyl group.

29. A compound of the formula

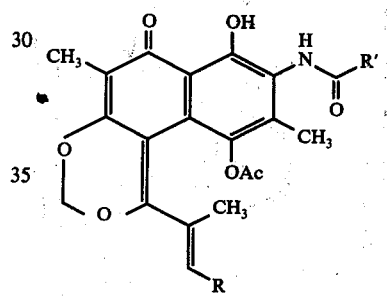

wherein

R IS [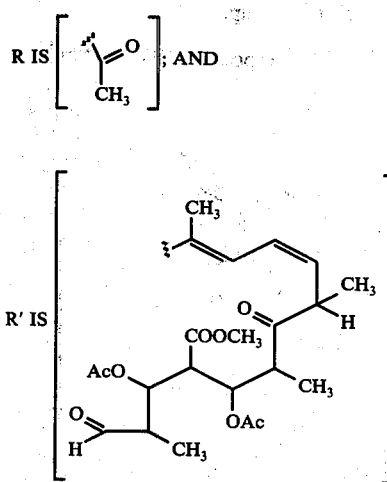] ; AND

R' IS and Ac is an acyl residue of a $C_2$ to $C_{18}$ carboxylic acid.

30. A compound according to claim 29 wherein Ac is an acetyl group.

31. A compound of the formula

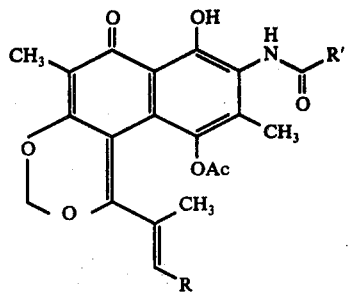

wherein

R IS 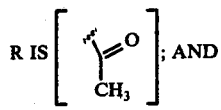 ; AND

R' IS 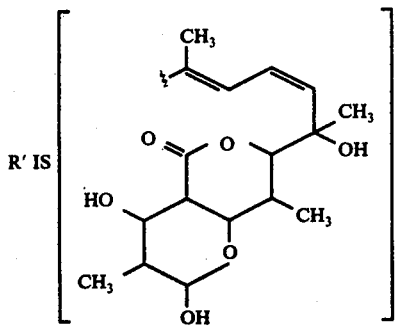

and Ac is an acyl residue of a $C_2$ to $C_{18}$ carboxylic acid.

32. A compound according to claim 31 wherein Ac is an acetyl group.

33. A compound of the formula

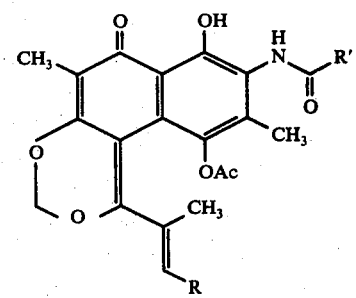

wherein

R IS 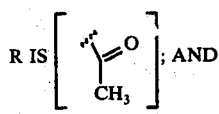 ; AND

R' IS 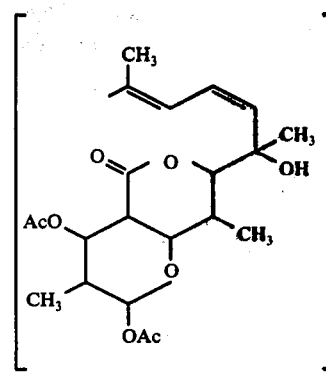

and Ac is an acyl residue of a $C_2$ to $C_{18}$ carboxylic acid.

34. A compound according to claim 33 wherein Ac is an acetyl group.

35. A compound of the formula

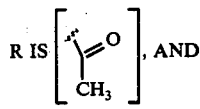

wherein

R IS [image of acetyl] , AND

R' IS [image of macrocyclic structure with AcO, OAc, OH, CH₃ groups]

and Ac is an acyl residue of a $C_2$ to $C_{18}$ carboxylic acid.

36. A compound according to claim 35 wherein Ac is an acetyl group.

37. A compound of the formula

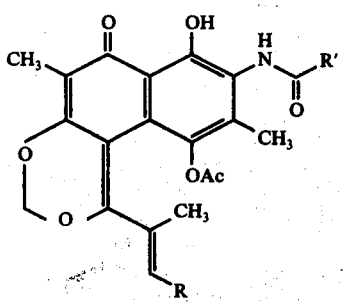

wherein

 ; AND

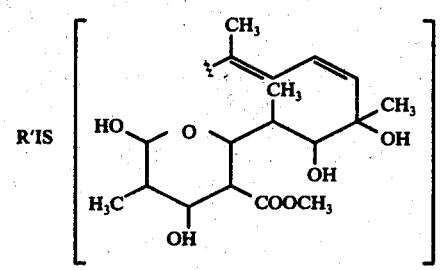

and Ac is an acyl residue of a $C_2$ to $C_{18}$ carboxylic acid.

38. A compound according to claim 37 wherein Ac is an acetyl group.

39. A compound of the formula

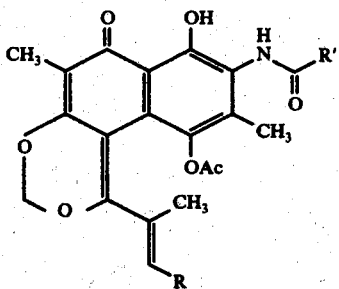

wherein

R IS 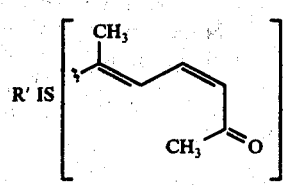 ; AND and Ac is an acyl residue of a $C_2$ to $C_{18}$ carboxylic acid.

40. A compound according to claim 39 wherein Ac is an acetyl group.

41. A compound of the formula

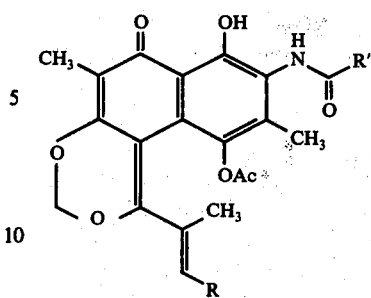

wherein

R IS  ; AND

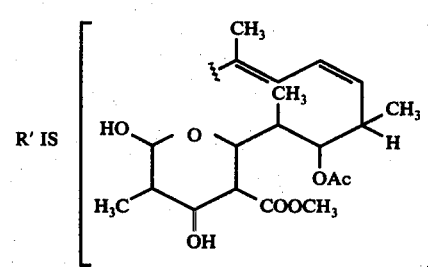

and Ac is an acyl residue of a $C_2$ to $C_{18}$ carboxylic acid.

42. A compound according to claim 41 wherein Ac is an acetyl group.

43. A compound of the formula

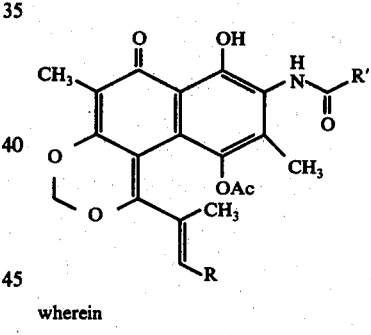

wherein

R IS  ; AND R' IS

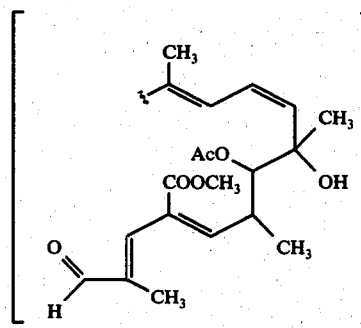

and Ac is an acyl residue of a $C_2$ to $C_{18}$ carboxylic acid.

44. A compound according to claim 43 wherein Ac is an acetyl group.

45. A compound of the formula

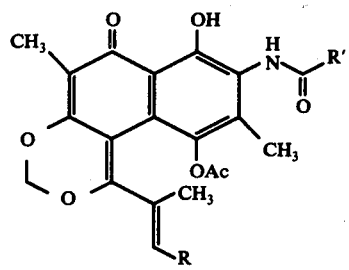

wherein

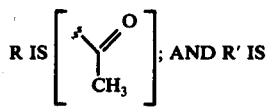

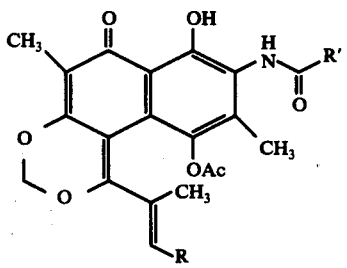

and Ac is an acyl residue of a $C_2$ to $C_{18}$ carboxylic acid.

46. A compound according to claim 45 wherein Ac is an acetyl group.

47. A compound of the formula

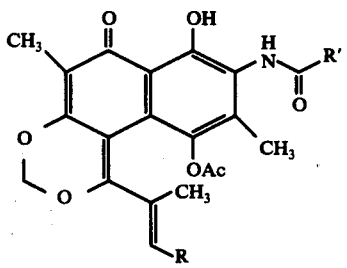

wherein

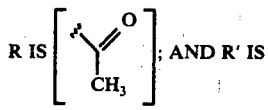

-continued

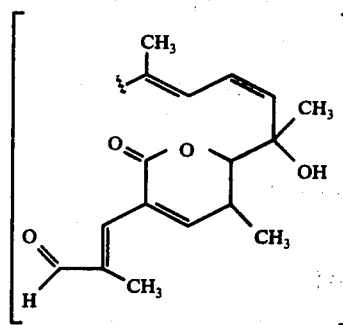

and Ac is an acyl residue of a $C_2$ to $C_{18}$ carboxylic acid.

48. A compound according to claim 47 wherein Ac is an acetyl group.

49. A compound of the formula

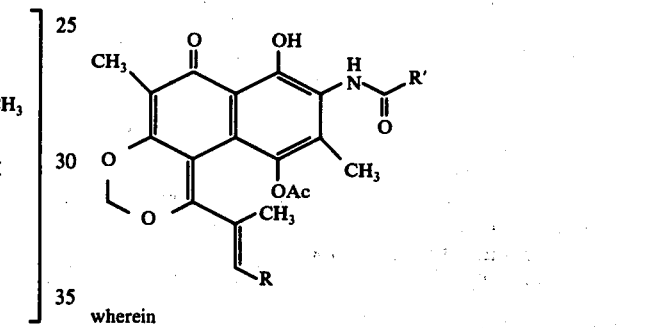

wherein

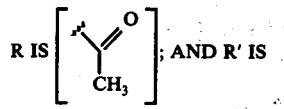

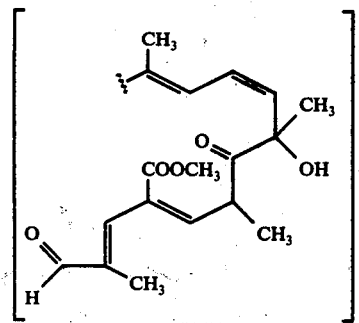

and Ac is an acyl residue of a $C_2$ to $C_{18}$ carboxylic acid.

50. A compound according to claim 49 wherein Ac is an acetyl group.

* * * * *

UNITED STATES PATENT AND TRADEMARK OFFICE
CERTIFICATE OF CORRECTION

PATENT NO. : 4,076,725

DATED : February 28, 1978

INVENTOR(S) : KENNETH L. RINEHART, JR., FREDERICK J. ANTOSZ, and KAZUYA SASAKI

It is certified that error appears in the above-identified patent and that said Letters Patent are hereby corrected as shown below:

Column 1, line 43, "and" should be --of--;

Column 1, line 63, "c" should be --C--;

Column 2, line 22, "conpounds" should be --compounds--;

Column 2, line 30, "process" should be --processes--;

Column 2, line 57, "S" should be --X--;

Column 3, line 19, "1957" should be --1959--;

Column 3, line 55, "w" should be --W--;

Column 4, line 23, "c" should be --$\underline{c}$--;

Column 4, line 40, "g" should be --G--;

Column 4, line 53, "a" should be --A--;

Column 5, line 15, "HMs" should be -- MHz --.

UNITED STATES PATENT AND TRADEMARK OFFICE
CERTIFICATE OF CORRECTION

PATENT NO. : 4,076,725

DATED : February 28, 1978

INVENTOR(S) : KENNETH L. RINEHART, JR., FREDERICK J. ANTOSZ, and KAZUYA SASAKI

It is certified that error appears in the above-identified patent and that said Letters Patent are hereby corrected as shown below:

Column 5, line 30, "CH-CH$_3$" first occurrence, should be --CH-C$\underline{H}_3$--;

Column 5, line 33, "(m,1,C=C$\underline{H}$-CH$_3$" should be --(m,1,C=CH-C$\underline{H}$-CH$_3$)-

Column 5, line 36, "S" should be --s--;

Column 5, line 40, "(M$^{30}$.)" should be --(M$^{+\cdot}$)--;

Column 5, line 46, "225" should be --255--;

Column 5, line 55, insert parenthesis [)] after v/v and before the comma [,];

Column 5, line 63, "CH$_3$" first occurrence, should be --C$\underline{H}_3$--;

Column 6, line 2, "(s,1,C=C-OH)" should be --(s,1,C=C-O$\underline{H}$)--;

Column 6, line 4, "CH$_3$" second occurrence, should be --C$\underline{H}_3$--;

Column 6, line 6, "2.47" should be --2.74--;

Column 6, line 11, "CH=CH-CH)" should be --CH=C$\underline{H}$-CH)--;

Column 6, line 33, "to" should read --of--;

Column 6, line 35, in title, "Streptovaricin D" should be --Streptovaricin B--;

Column 6, line 69, "conbined" should be --combined--;

UNITED STATES PATENT AND TRADEMARK OFFICE
CERTIFICATE OF CORRECTION

PATENT NO. : 4,076,725
DATED : February 28, 1978
INVENTOR(S) : KENNTH L. RINEHART, JR., FREDERICK J. ANTOSZ, and KAZUYA SASAKI It is certified that error appears in the above-identified patent and that said Letters Patent are hereby corrected as shown below:

Column 7, line 41, "Streptovarican" should be --Streptovaricin--;

Column 12, line 41, "solution" should be --suspension--;

Column 12, line 56, "perperative" should be --preparative--;

Column 13, line 13, "C$\underline{H}$=CH-CH)," should be --CH=C$\underline{H}$-CH),--;

Column 15, line 35, "oil" should read --oily--;

Column 15, line 46, "was" first occurrence, should be --which--;

Column 19, line 16, "5,5-5.9" should be --5.5-5.9--;

Column 20, line 67, "mens" should be --means--;

Column 21, line 16, "(36;1)" should be --(36)--;

Column 22, line 58, "mecahanically" should be --mechanically--;

Column 23, line 51, after "fractions" delete the period (.);

Column 24, line 6, "in acuo" should be --in vacuo--;

Column 26, top formula, about line 7, "$A_cO$" should be --AcO--;

Column 26, line 25, "$A_cO$" should be --AcO--;

Column 27, line 5, "diacetate-B) Formula 7)" should be --diacetate-B (Formula 7)--;

UNITED STATES PATENT AND TRADEMARK OFFICE
CERTIFICATE OF CORRECTION

PATENT NO. : 4,076,725

DATED : February 28, 1978

INVENTOR(S) : KENNETH L. RINEHART, JR., FREDERICK J. ANTOSZ, and KAZUYA SASAKI

It is certified that error appears in the above-identified patent and that said Letters Patent are hereby corrected as shown below:

Column 28, line 24, "J. Bacterial" should be --J. Bacteriol.--;

Column 32, line 21, "r" should be --R--;

Column 33, lines 43-48 should read

AND $R^1$ IS 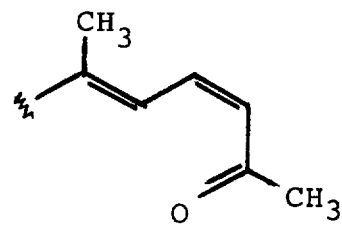 ;

Column 36, lines 7-17 should read

AND $R^1$ IS 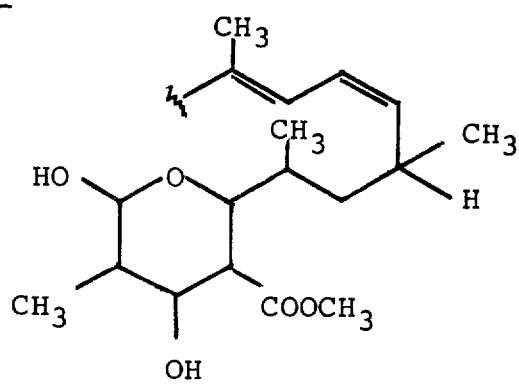 ;

UNITED STATES PATENT AND TRADEMARK OFFICE
CERTIFICATE OF CORRECTION

PATENT NO. : 4,076,725
DATED : February 28, 1978
INVENTOR(S) : KENNETH L. RINEHART, JR., FREDERICK J. ANTOSZ, and KAZUYA SASAKI It is certified that error appears in the above-identified patent and that said Letters Patent are hereby corrected as shown below:

Column 36, lines 57-68, should read

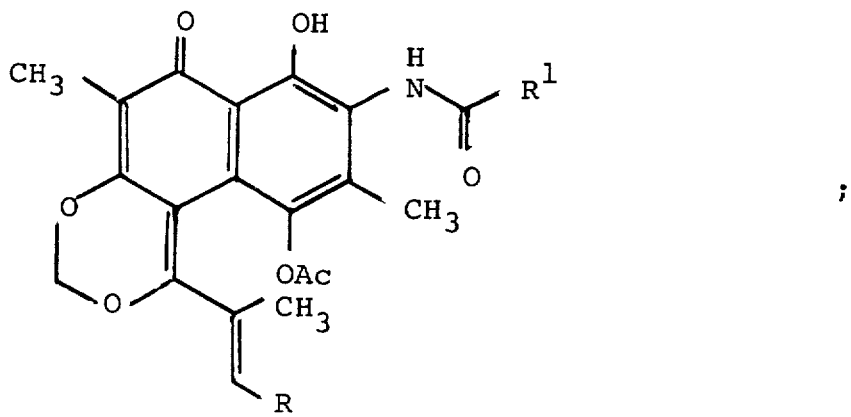

;

Column 44, line 21, "a compound" should be --A compound--.

Signed and Sealed this

Fifteenth Day of August 1978

[SEAL]

Attest:

RUTH C. MASON
Attesting Officer

DONALD W. BANNER
Commissioner of Patents and Trademarks